US012692316B2

(12) United States Patent
Morsey et al.

(10) Patent No.: US 12,692,316 B2
(45) Date of Patent: Jul. 28, 2026

(54) ANTIBODIES TO CANINE INTERLEUKIN-4 RECEPTOR ALPHA

(71) Applicant: Intervet Inc., Madison, NJ (US)

(72) Inventors: Mohamad Morsey, Omaha, NE (US); Yuanzheng Zhang, Somerset, NJ (US)

(73) Assignee: INTERVET INC., Rahway, NJ (US)

( * ) Notice: Subject to any disclaimer, the term of this patent is extended or adjusted under 35 U.S.C. 154(b) by 867 days.

(21) Appl. No.: 17/784,835

(22) PCT Filed: Dec. 18, 2020

(86) PCT No.: PCT/EP2020/086919
§ 371 (c)(1),
(2) Date: Jun. 13, 2022

(87) PCT Pub. No.: WO2021/123089
PCT Pub. Date: Jun. 24, 2021

(65) Prior Publication Data

US 2023/0053131 A1 Feb. 16, 2023

Related U.S. Application Data

(60) Provisional application No. 63/015,220, filed on Apr. 24, 2020, provisional application No. 63/015,209, filed on Apr. 24, 2020, provisional application No. 62/951,778, filed on Dec. 20, 2019, provisional application No. 62/951,793, filed on Dec. 20, 2019.

(51) Int. Cl.

| | |
|---|---|
| ***C07K 16/28*** | (2006.01) |
| ***A61K 39/395*** | (2006.01) |
| ***A61P 17/00*** | (2006.01) |
| ***C12N 5/071*** | (2010.01) |
| ***C12N 15/85*** | (2006.01) |

(52) U.S. Cl.
CPC .......... *C07K 16/2866* (2013.01); *A61P 17/00* (2018.01); *C12N 5/0602* (2013.01); *C12N 15/85* (2013.01); *A61K 39/3955* (2013.01); *C07K 2317/24* (2013.01); *C07K 2317/34* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 7,208,579 B2 | 4/2007 | Watson et al. | |
| 8,790,651 B2 | 7/2014 | Bammert et al. | |
| 10,093,731 B2 | 10/2018 | Li et al. | |
| 10,106,607 B2 | 10/2018 | Morsey et al. | |
| 2015/0017176 A1 | 1/2015 | Kostic et al. | |
| 2018/0346580 A1 | 12/2018 | Morsey et al. | |
| 2018/0371097 A1 | 12/2018 | Morsey et al. | |
| 2023/0044037 A1* | 2/2023 | Morsey | C12N 5/0602 |
| 2023/0250177 A1* | 8/2023 | Morsey | A61P 37/08 424/130.1 |
| 2023/0295289 A1* | 9/2023 | Morsey | A61P 17/00 424/145.1 |

FOREIGN PATENT DOCUMENTS

| | | |
|---|---|---|
| CN | 107683291 A | 2/2018 |
| JP | 2018511322 A | 4/2018 |
| RU | 2679920 C2 | 2/2019 |
| WO | WO 2014197470 A1 | 12/2014 |
| WO | 2016156588 A1 | 10/2016 |
| WO | 2017102920 A1 | 6/2017 |

OTHER PUBLICATIONS

Ahmed et al., 2015, "Identification and Characterization of a Novel IL-4 Receptor α Chain (IL-4Rα) Antagonist to Inhibit IL-4 Signal-ling," Cell Physiol. Biochem., 36(3):831-842.
Bergeron et al., Comparative functional characterization of canine IgG subclasses, Veterinary Immunology and Immunopathology, 2014, pp. 31-41, 157.
Chothia and Lesk et al, Canonical Structures for the Hypervariable Regions of Immunoglobins, J. Mol. Biol., 1987, 901-917, 196.
Chothia et al., Conformations of immunoglobin hypervariable regions, Nature, 1989, 877-883, 342.
Gelebart, Pascal and Lai, Raymond, IL22RA1 (interleukin 22 receptor, alpha 1), Atlas of Genetics and Cytogenetics in Oncology and Haematology, 2010, 1106-1110, 14(12).
Harskamp et al., Immunology of Atopic Dermatitis: Novel Insights into Mechanisms and Immunomodulatory Therapies, Seminars in Cutaneous Medicine and Surgery, 2013, 132-139, 32.
Huber, Samuel et al., IL-22BP is regulated by the inflammasome and modulates tumorigenesis in the intestine, Nature, 2012, 259-263, 491.
Kabat, the Structural Basis of Antibody Complementarity, Adv. Prot. Chem., 1978, 1-75, 32.
Kabat, Unusual Distributions of Amino Acids in Complementarity-determining (Hypervriable) Segment of Heavy and Light Chains of Immunoglobulins and Their Possible Roles in Specificity of Antibody-combining Sites, J. Biol. Chem., 1977, 6609-6616, 252.
Lee, Donna W. et al., Nonclinical safety assessment of a human interleukin-22FC IG fusion protein demonstrates in vitro to in vivo and cross-species translatability, Pharmacol Res Perspect., 2018, 1-13, e00434.

(Continued)

*Primary Examiner* — Ilia I Ouspenski
(74) *Attorney, Agent, or Firm* — JONES DAY

(57) ABSTRACT

The present invention provides antibodies to canine IL-4 receptor alpha that have a high binding affinity for canine IL-4 receptor alpha, and that can block the binding of canine IL-4 and/or IL-13 to canine IL-4 receptor alpha. The present invention further relates to epitopes of canine IL-4 receptor alpha that bind to the antibodies to canine IL-4 receptor alpha. The present invention further provides the use of the antibodies for the treatment of atopic dermatitis in dogs.

20 Claims, 2 Drawing Sheets

Specification includes a Sequence Listing.

(56) References Cited

OTHER PUBLICATIONS

Morrison, Sherie L. et al., Chimeric human antibody molecules: Mouse antigen-binding domains with human constant region domains, Proc. Natl. Acad. Sci. USA, 1984, 6851-6855, 81.
Nuttall et al., Canine Atopic Dermatitis—what have we learned?, Veterinary Record, 2013, 201-207, 172(8).
Rahman et al., The Pathology and Immunology of Atopic Dermatitis, Inflammation & Allergy—Drug Targets, 2011, 186-496, 10.
Ruzicka, Thomas et al., Anti-Interleukin-31 Receptor A Antibody for Atopic Dermatitis, The New England Journal of Medicine, 2017, 826-835, 376(9).
Tang et al., Cloning and characterization of cDNAs encoding four different canine immunoglobulin Y chains, Veterinary Immunology and Immunopathology, 2001, pp. 259-270, 80.
Xu, Wenfeng et al., A soluble class II cytokine receptor, IL-22RA2, is a naturally occurring IL-22 antagonist, PNAS, 2001, 9511-9516, vol. 98 | No. 17.

* cited by examiner

Figure 1. Inhibition of IL-4 mediated STAT-6 phosphorylation by antibodies to canine IL-4 receptor alpha
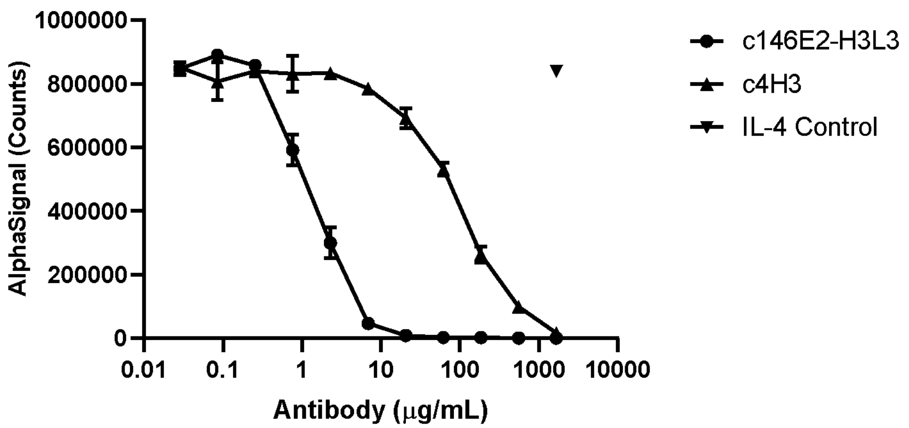
Figure 2. Inhibition of IL-13 mediated STAT-6 phosphorylation by antibodies to canine IL-4 receptor alpha
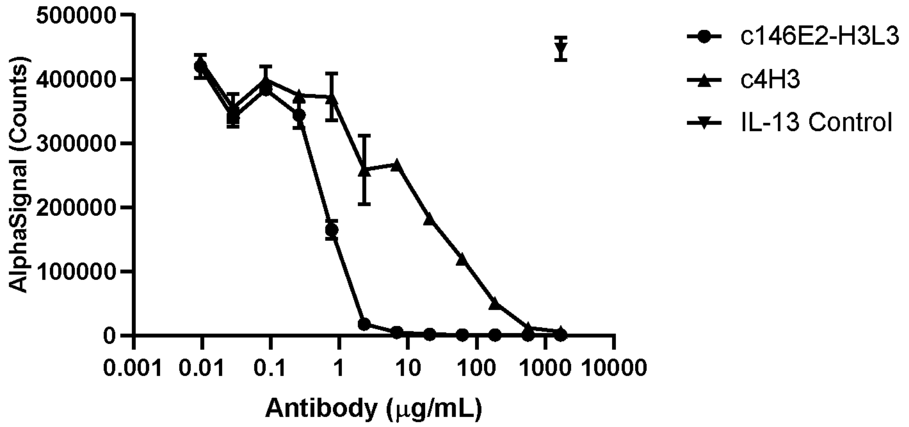

| | 146 mc | 146CL1-H1 | 146CL1-H2 | 146CL1-H3 | 146CkL3-H3 | Iso-ctrl |
|---|---|---|---|---|---|---|
| EC50 | 2.042 | 2.181 | 1.498 | 1.281 | 1.760 | ~ |

ANTIBODIES TO CANINE INTERLEUKIN-4 RECEPTOR ALPHA

CROSS-REFERENCE TO RELATED APPLICATIONS

This application is a National Stage application of International Patent Application No. PCT/EP2020/086919 filed Dec. 18, 2020, which claims priority to U.S. Provisional Patent Application No. 63/015,209, filed Apr. 24, 2020, U.S. Provisional Patent Application No. 63/015,220, filed Apr. 24, 2020, U.S. Provisional Patent Application No. 63/951,793, filed Dec. 20, 2019 and U.S. Provisional Patent Application No. 62/951,778, filed Dec. 20, 2019, the contents of all of which are hereby incorporated by reference in their entireties

SEQUENCE LISTING

This application incorporates by reference in its entirety the Computer Readable Form (CRF) of a Substitute Sequence Listing in ASCII text format submitted via Patent Center. The Substitute Sequence Listing text file submitted via Patent Center is entitled "14463-268-999 SUB_SL.txt," was created on Jun. 20, 2025, and is 64,562 bytes in size.

FIELD OF THE INVENTION

The present invention relates to antibodies to canine IL-4 receptor alpha that have a high binding affinity for canine IL-4 receptor alpha, and that can block the binding of canine IL-4 and/or IL-13 to canine IL-4 receptor alpha. The present invention also relates to use of the antibodies of the present invention in the treatment of atopic dermatitis in dogs.

BACKGROUND OF THE INVENTION

The immune system comprises a network of resident and recirculating specialized cells that function collaboratively to protect the host against infectious diseases and cancer. The ability of the immune system to perform this function depends to a large extent on the biological activities of a group of proteins secreted by leukocytes and collectively referred to as interleukins. Among the well-studied interleukins are four important molecules identified as interleukin-4 (IL-4), interleukin-13 (IL-13), interleukin-31 (IL-31), and interleukin-22 (IL-22). IL-4 and IL-13 are closely related proteins that can be secreted by many cell types including $CD4^+$ Th2 cells, natural killer T cells (NKT), macrophages, mast cells, and basophils. IL-4 and IL-13 display many overlapping functions and are critical to the development of T cell-dependent humoral immune responses. It is known that IL-4 binds with high affinity to two receptors i.e., type-I and type-II IL-4 receptors. The type I IL-4 receptor consists of the IL-4 receptor α chain and the common γ C chain. The Type II IL-4 receptor consists of the IL-4 receptor α chain and the IL-13 receptor α1 chain. IL-13 binds to the type-II IL-4 receptor, and to a unique receptor designated IL-13 receptor α2. The binding of IL-13 to the IL-13 receptor α2 does not transduce a signal and this receptor is also secreted in a soluble form. Accordingly, the IL-13 receptor α2 has often been referred to as a decoy receptor. Although IL-4, IL-13, IL-22, and IL-31, are critical cytokines for the development of immune responses that are required for protection against extracellular pathogens (e.g., tissue or lumen dwelling parasites), these cytokines also have been implicated in the pathogenesis of allergic diseases in humans and animals, including atopic dermatitis.

Atopic dermatitis (AD) is a relapsing pruritic and chronic inflammatory skin disease, that is characterized by immune system dysregulation and epidermal barrier abnormalities in humans. The pathological and immunological attributes of atopic dermatitis have been the subject of extensive investigations [reviewed in Rahman et al. *Inflammation & Allergy-drug target* 10:486-496 (2011) and Harskamp et al., *Seminar in Cutaneous Medicine and Surgery* 32:132-139 (2013)]. Atopic dermatitis is also a common condition in companion animals, especially dogs, where its prevalence has been estimated to be approximately 10-15% of the canine population. The pathogenesis of atopic dermatitis in dogs and cats [reviewed in Nuttall et al., *Veterinary Records* 172(8):201-207 (2013)] shows significant similarities to that of atopic dermatitis in man including skin infiltration by a variety of immune cells and $CD4^+$ Th2 polarized cytokine milieu including the preponderance of IL-4, IL-13, and IL-31. In addition, IL-22 has been implicated in the exaggerated epithelial proliferation leading to epidermal hyperplasia that is characteristic of atopic dermatitis.

For example, antibodies against canine IL-31 have been shown to have a significant effect on pruritus associated with atopic dermatitis in dogs [U.S. Pat. No. 8,790,651 B2; U.S. Pat. No. 10,093,731 B2]. In addition, an antibody against human IL-31 receptor alpha (IL-31RA) has been tested and found to have a significant effect on pruritus associated with atopic dermatitis in humans [Ruzicka, et al., *New England Journal of Medicine,* 376(9), 826-835 (2017)]. Accordingly, blocking IL-31 binding to its receptor IL-31RA, results in the relief of pruritus associated with atopic dermatitis.

Monoclonal antibodies raised against human IL-4 receptor alpha (IL-4 $R_\alpha$) have been developed and some of these antibodies have been extensively tested for their therapeutic effects for treating atopic dermatitis in humans [see, e.g., US2015/0017176 A1]. More recently, caninized antibodies to canine IL-4 $R_\alpha$ that block the binding of canine IL-4 to canine IL-4 $R_\alpha$ also have been disclosed [US2018/0346580A1, hereby incorporated by reference in its entirety]. Because the Type II IL-4 receptor consists of the IL-4 receptor α chain and the IL-13 receptor α1 chain, antibodies to canine IL-4 $R_\alpha$ have been obtained that can block both canine IL-4 and canine IL-13 from binding the Type II canine IL-4 receptor, thereby serving to help block the inflammation associated with atopic dermatitis [US2018/0346580A1].

Interleukin-22 (IL-22), also known as IL-10-related T cell-derived inducible factor (IL-TIF), belongs to the IL-10 cytokine family. IL-22 is produced by normal T cells upon anti-CD3 stimulation in humans. Mouse IL-22 expression is also induced in various organs upon lipopolysaccharide injection, suggesting that IL-22 may be involved in inflammatory responses. IL-22 binds specifically to, and signals through, a receptor complex consisting of a heterodimeric complex of IL-10R2 (also known as IL-10R beta) and the Interleukin-22 receptor (IL-22R) [see, Lee et al., *Pharmacology Research & Perspectives*, Pages 1-13 (2018. e00434)]. The Interleukin-22 receptor is also known as Interleukin-22R, alpha 1; IL-22RA1; IL-22R1; zcytor11; and CRF2-9 [Xu et al., *Proc. Nat. Acad. Sci.* 98 (17) 9511-9516 (2001), Gelebart and Lai, *Atlas of Genetics and Cytogenetics* 14(12). 1106-1110 (2010)] IL-22 induces epithelial cell proliferation during wound healing, and its deficiency can enable uncontrolled proliferation and enhance tumor development [Huber et al., *Nature* 491:259-263 (2012]. IL-22 has been shown to activate STAT-1 and STAT-3 in several hepatoma cell lines and upregulate the production of acute phase proteins. Antibodies to Interleukin-22 and IL-22R act as anti-proliferative agents by blocking the interaction of IL-22 with IL-22R and thereby the related signaling pathway that leads to the epithelial proliferation.

However, despite recent success in treating atopic dermatitis, none of the current therapies employed result in a rapid onset of antipruritic action concomitant with a significant effect on the skin inflammation with an improvement in skin barrier function. Therefore, there is a need to design better therapies that can address one or more of the symptoms of atopic dermatitis.

The citation of any reference herein should not be construed as an admission that such reference is available as "prior art" to the instant application.

SUMMARY OF THE INVENTION

The present invention provides new caninized antibodies to canine IL-4R alpha (IL-4$R_\alpha$), which in particular embodiments are isolated, that have superior properties than those in the prior art, e.g., binding more tightly than prior art anti-canine IL-4 receptor alpha antibodies. In particular embodiments, the present invention provides mammalian antibodies or antigen binding fragments thereof that bind the canine interleukin-4 receptor alpha with specificity comprising a heavy chain that comprises a set of three heavy chain complementary determining regions (CDRs), a CDR heavy 1 (HCDR1), a CDR heavy 2 (HCDR2), and a CDR heavy 3 (HCDR3) in which the HCDR1 comprises the amino acid sequence of SEQ ID NO: 12, the HCDR2 comprises the amino acid sequence of SEQ ID NO: 14, and the HCDR3 comprises the amino acid sequence of SEQ ID NO: 16. In related embodiments the mammalian antibodies or antigen binding fragments thereof that bind the canine interleukin-4 receptor α (IL-4$R_\alpha$) with specificity further comprise a light chain that comprises a set of three light chain CDRs: a CDR light 1 (LCDR1), a CDR light 2 (LCDR2), and a CDR light 3 (LCDR3), in which the LCDR1 comprises the amino acid sequence of SEQ ID NO: 18, the LCDR2 comprises the amino acid sequence of SEQ ID NO: 20, and the LCDR3 comprises the amino acid sequence of SEQ ID NO: 22. In preferred embodiments the mammalian antibody or antigen binding fragment thereof bind canine IL-4$R_\alpha$ and block the binding of canine IL-4$R_\alpha$ to canine interleukin-4 (cIL-4). In related embodiments the mammalian antibody or antigen binding fragment thereof bind canine IL-4$R_\alpha$ and block the binding of canine IL-4$R_\alpha$ to canine interleukin-13 (cIL-13). In still other embodiments, the mammalian antibody or antigen binding fragment thereof bind canine IL-4$R_\alpha$ and block the binding of canine IL-4$R_\alpha$ to cIL-4 and to cIL-13.

In specific embodiments the mammalian antibody to canine IL-4R alpha is a murine antibody. In related embodiments, the mammalian antibody to canine IL-4R alpha is a caninized murine antibody. In particular embodiments, the caninized antibody comprises a heavy chain that comprises an IgG-D cFc, but the naturally occurring IgG-D hinge region is replaced by a hinge region comprising the amino acid sequence of SEQ ID NO: 6. In other embodiments, the caninized antibody comprises a heavy chain that comprises an IgG-D cFc, but the naturally occurring IgG-D hinge region is replaced by a hinge region comprising the amino acid sequence of SEQ ID NO: 7. In still other embodiments, the caninized antibody comprises a heavy chain that comprises an IgG-D cFc, but the naturally occurring IgG-D hinge region is replaced by a hinge region comprising the amino acid sequence of SEQ ID NO: 8. In yet other embodiments, the caninized antibody comprises a heavy chain that comprises an IgG-D cFc, but the naturally occurring IgG-D hinge region is replaced by a hinge region comprising the amino acid sequence of SEQ ID NO: 9.

In specific embodiments, the caninized antibody comprises a heavy chain comprising a modified canine IgG-B (IgG-Bm) that comprises the amino acid sequence of SEQ ID NO: 10. In certain embodiments, the caninized antibody comprises a heavy chain that comprises the amino acid sequence SEQ ID NO: 40. In other embodiments, the caninized antibody comprises a heavy chain that comprises the amino acid sequence SEQ ID NO: 41. In still other embodiments, the caninized antibody comprises a heavy chain that comprises the amino acid sequence SEQ ID NO: 42. In specific embodiments, the caninized antibody further comprises a light chain that comprises the amino acid sequence SEQ ID NO: 39. In alternative embodiments, the caninized antibody further comprises a light chain that comprises the amino acid sequence SEQ ID NO: 44.

In particular embodiments, the caninized antibodies or antigen binding fragments thereof bind to SEQ ID NO: 46. In more particular embodiments, the caninized antibodies or antigen binding fragments thereof bind to one, two, or all three of the following amino acid residues of canine IL-4$R_\alpha$: $K_{97}$, $H_{112}$, $T_{113}$ of SEQ ID NO: 5. In related embodiments, the caninized antibodies or antigen binding fragments thereof bind to SEQ ID NO: 47. In more particular embodiments, the caninized antibodies or antigen binding fragments thereof bind to one, two, three, four or all five of the following amino acid residues of canine IL-4$R_\alpha$: $S_{164}$, $T_{165}$, $S_{171}$, $Y_{172}$, $S_{173}$, and $R_{175}$ of SEQ ID NO: 5. In still more particular embodiments, the caninized antibodies or antigen binding fragments thereof bind to both SEQ ID NO: 46 and SEQ ID NO: 47. In yet more particular embodiments of this type, the caninized antibodies or antigen binding fragments thereof bind to one, two, or all three of the following amino acid residues of canine IL-4$R_\alpha$: $K_{97}$, $H_{112}$, $T_{113}$ of SEQ ID NO: 5 and/or to one, two, three, four or all five of the following amino acid residues of canine IL-4$R_\alpha$: $S_{164}$, $T_{165}$, $S_{171}$, $Y_{172}$, $S_{173}$, and $R_{175}$ of SEQ ID NO: 5.

The present invention also provides nucleic acids, including isolated nucleic acids, that encode the CDRs, the heavy chains of the caninized antibodies or antigen binding fragments thereof, and/or the light chains of the caninized antibodies or antigen binding fragments thereof. In addition, the present invention provides expression vectors that comprise such nucleic acids, and host cells that comprise such expression vectors.

In addition, the present invention provides pharmaceutical compositions that comprise the caninized antibodies and antigen binding fragments thereof of the present invention along with a pharmaceutically acceptable carrier and/or diluent. The present invention further provides methods of treating atopic dermatitis comprising administering one of the aforesaid compositions to a canine that has atopic dermatitis. In particular embodiments, the present invention provides methods of aiding in the blocking of inflammation associated with atopic dermatitis, comprising administering to a canine in need thereof a therapeutically effective amount of a pharmaceutical composition of the present invention.

These and other aspects of the present invention will be better appreciated by reference to the following Brief Description of the Drawings and the Detailed Description.

BRIEF DESCRIPTION OF THE DRAWINGS

FIG. 1 shows two different caninized monoclonal anti-canine interleukin-4 receptor, alpha antibodies designated c4H3 [see, WO2016/156588] and c146E2-H3L3 which were evaluated for their ability to inhibit STAT-6 phosphorylation. The data shows that both antibodies result in a dose dependent inhibition of STAT-6 phosphorylation in the presence of canine interleukin-4. The IL-4 control in the absence of IL-4R alpha (IL-4$R_{\alpha}$) antibodies is shown in the upper right-hand portion of the graph.

FIG. 2 shows two different caninized monoclonal anti-canine interleukin-4 receptor, alpha antibodies designated c4H3 [see, WO2016/156588] and c146E2-H3L3, which were evaluated for their ability to inhibit STAT-6 phosphorylation. The data shows that both antibodies result in a dose dependent inhibition of STAT-6 phosphorylation in the presence of canine interleukin-13. The IL-13 control in the absence of IL-4R alpha (IL-4$R_{\alpha}$) antibodies is shown in the upper right-hand portion of the graph.

DETAILED DESCRIPTION OF THE INVENTION

Figure 3:
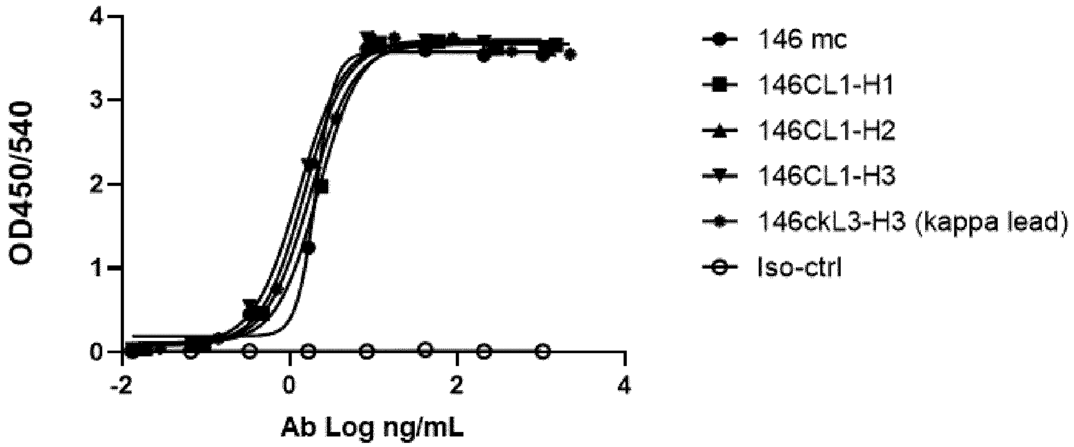
FIG. 3 shows the binding of caninized anti-canine IL-4$R_{\alpha}$ antibodies containing either lambda or kappa light chains as evaluated by ELISA. The results show that caninized anti-canine IL-4$R_{\alpha}$ antibodies containing lambda light chains (c146ClL1-H1, c146ClL1-H2 and c146ClL1-H3) bind to canine IL-4$R_{\alpha}$ as well as caninized anti-canine IL-4$R_{\alpha}$ antibodies containing the same CDRs, but with a kappa light chain (c146E2-H3L3). 146 mc is the mouse-canine chimeric antibody positive control and Iso-Ctr, the negative control, is an unrelated caninized antibody.

In response to need for better therapies for atopic dermatitis, the present invention provides caninized antibodies, formulations with the caninized antibodies, and methodologies that can achieve a significant effect on the skin inflammation associated with atopic dermatitis.

Abbreviations

Throughout the detailed description and examples of the invention the following abbreviations will be used:

ADCC Antibody-dependent cellular cytotoxicity

CDC Complement-dependent cyotoxicity

CDR Complementarity determining region in the immunoglobulin variable regions, defined using the Kabat numbering system EC50 concentration resulting in 50% efficacy or binding ELISA Enzyme-linked immunosorbant assay FR Antibody framework region: the immunoglobulin variable regions excluding the CDR regions.

IC50 concentration resulting in 50% inhibition

IgG Immunoglobulin G

Kabat An immunoglobulin alignment and numbering system pioneered by Elvin A. Kabat [*Sequences of Proteins of Immunological Interest,* 5th Ed. Public Health Service, National Institutes of Health, Bethesda, Md. (1991)]

mAb Monoclonal antibody (also Mab or MAb)

V region The segment of IgG chains which is variable in sequence between different antibodies. It extends to Kabat residue 109 in the light chain and 113 in the heavy chain.

VH Immunoglobulin heavy chain variable region

VL Immunoglobulin light chain variable region

VK Immunoglobulin kappa light chain variable region

Definitions

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as “a,” “an,” and “the,” include their corresponding plural references unless the context clearly dictates otherwise.

“Administration” and “treatment”, as it applies to an animal, e.g., a canine subject, cell, tissue, organ, or biological fluid, refers to contact of an exogenous pharmaceutical, therapeutic, diagnostic agent, or composition to the animal e.g., a canine subject, cell, tissue, organ, or biological fluid. Treatment of a cell encompasses contact of a reagent to the cell, as well as contact of a reagent to a fluid, where the fluid is in contact with the cell.

“Administration” and “treatment” also mean in vitro and ex vivo treatments, e.g., of a cell, by a reagent, diagnostic, binding compound, or by another cell. The term “subject” includes any organism, preferably an animal, more preferably a mammal (e.g., canine, feline, or human) and most preferably a canine.

“Treat” or “treating” means to administer a therapeutic agent, such as a composition containing any of the antibodies of the present invention, internally or externally to e.g., a canine subject or patient having one or more symptoms, or being suspected of having a condition, for which the agent has therapeutic activity. Typically, the agent is administered in an amount effective to alleviate and/or ameliorate one or more disease/condition symptoms in the treated subject or population, whether by inducing the regression of or inhibiting the progression of such symptom(s) by any clinically measurable degree. The amount of a therapeutic agent that is effective to alleviate any particular disease/condition symptom (also referred to as the “therapeutically effective amount”) may vary according to factors such as the disease/condition state, age, and weight of the patient (e.g., canine), and the ability of the pharmaceutical composition to elicit a desired response in the subject. Whether a disease/condition symptom has been alleviated or ameliorated can be assessed by any clinical measurement typically used by veterinarians or other skilled healthcare providers to assess the severity or progression status of that symptom. While an embodiment of the present invention (e.g., a treatment method or article of manufacture) may not be effective in alleviating the target disease/condition symptom(s) in every subject, it should alleviate the target disease/condition symptom(s) in a statistically significant number of subjects as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

“Treatment,” as it applies to a human, veterinary (e.g., canine), or research subject, refers to therapeutic treatment, as well as research and diagnostic applications. “Treatment” as it applies to a human, veterinary (e.g., canine), or research subject, or cell, tissue, or organ, encompasses contact of the antibodies of the present invention to e.g., a canine or other animal subject, a cell, tissue, physiological compartment, or physiological fluid.

As used herein, the term "canine" includes all domestic dogs, Canis lupus familiaris or Canis familiaris, unless otherwise indicated.

As used herein, the term "feline" refers to any member of the Felidae family. Members of this family include wild, zoo, and domestic members, including domestic cats, pure-bred and/or mongrel companion cats, show cats, laboratory cats, cloned cats, and wild or feral cats.

As used herein the term "canine frame" refers to the amino acid sequence of the heavy chain and light chain of a canine antibody other than the hypervariable region residues defined herein as CDR residues. With regard to a caninized antibody, in the majority of embodiments the amino acid sequences of the native canine CDRs are replaced with the corresponding foreign CDRs (e.g., those from a mouse antibody) in both chains. Optionally the heavy and/or light chains of the canine antibody may contain some foreign non-CDR residues, e.g., so as to preserve the conformation of the foreign CDRs within the canine antibody, and/or to modify the Fc function, as exemplified below and/or disclosed in U.S. Pat. No. 10,106,607 B2, hereby incorporated by reference herein in its entirety.

The "Fragment crystallizable region" abbreviated as "Fc" corresponds to the CH3-CH2 portion of an antibody that interacts with cell surface receptors called Fc receptors. The canine fragment crystallizable region (cFc) of each of the four canine IgGs were first described by Tang et al. [*Vet. Immunol. Immunopathol.* 80: 259-270 (2001); see also, Bergeron et al., *Vet. Immunol. Immunopathol.* 157: 31-41 (2014) and U.S. Pat. No. 10,106,607 B2].

As used herein the canine Fc (cFc) "IgG-Bm" is canine IgG-B Fc comprising two (2) amino acid residue substitutions, D31A and N63A in the amino acid sequence of SEQ ID NO: 10 of IgG-B (see below) and without the c-terminal lysine ('K"). Both the aspartic acid residue (D) at position 31 of SEQ ID NO: 10 and the asparagine residue (N) at position 63 of SEQ ID NO: 10, are substituted by an alanine residue (A) in IgG-Bm. These two amino acid residue substitutions serve to significantly diminish the antibody-dependent cytotoxicity (ADCC) and complement-dependent cytotoxicity (CDC) of the naturally occurring canine IgG-B [see, U.S. Pat. No. 10,106,607 B2, the contents of which are hereby incorporated by reference in their entirety]. Further amino acid substitutions to the IgG-Bm are also envisioned, which parallel those which can be made in IgG-B and may include amino acid substitutions to favor heterodimer formation in bispecific antibodies. The amino acid sequence of IgG-B, SEQ ID NO: 45 is:

```
1                                                   50
LGGPSVFIFP PKPKDTLLIA RTPEVTCVVV DLDPEDPEVQ ISWFVDGKQM
      CH2

51                                                 100
QTAKTQPREE QFNGTYRVVS VLPIGHQDWL KGKQFTCKVN NKALPSPIER

101                                                150
TISKARGQAH QPSVYVLPPS REELSKNTVS LTCLIKDFFP PDIDVEWQSN
             CH3

151                                                200
GQQEPESKYR TTPPQLDEDG SYFLYSKLSV DKSRWQRGDT FICAVMHEAL

201            215
HNHYTQKSLS HSPGK
```

The amino acid sequence of IgG-Bm, SEQ ID NO: 10, is provided below.

```
LGGPSVFIFPPKPKDTLLIARTPEVTCVVVALDPEDPEVQISWEVDGKQ

MQTAKTQPREEQFAGTYRVVSVLPIGHQDWLKGKQFTCKVNNKALPSPI

ERTISKARGQAHQPSVYVLPPSREELSKNTVSLTCLIKDFFPPDIDVEW

QSNGQQEPESKYRTTPPQLDEDGSYFLYSKLSVDKSRWQRGDTFICAVM

HEALHNHYTQESLSHSPG
```

As used herein, a "substitution of an amino acid residue" with another amino acid residue in an amino acid sequence of an antibody for example, is equivalent to "replacing an amino acid residue" with another amino acid residue and denotes that a particular amino acid residue at a specific position in the amino acid sequence has been replaced by (or substituted for) by a different amino acid residue. Such substitutions can be particularly designed i.e., purposefully replacing an alanine with a serine at a specific position in the amino acid sequence by e.g., recombinant DNA technology. Alternatively, a particular amino acid residue or string of amino acid residues of an antibody can be replaced by one or more amino acid residues through more natural selection processes e.g., based on the ability of the antibody produced by a cell to bind to a given region on that antigen, e.g., one containing an epitope or a portion thereof, and/or for the antibody to comprise a particular CDR that retains the same canonical structure as the CDR it is replacing. Such substitutions/replacements can lead to "variant" CDRs and/or variant antibodies.

As used herein, the term "antibody" refers to any form of antibody that exhibits the desired biological activity. An antibody can be a monomer, dimer, or larger multimer. Thus, it is used in the broadest sense and specifically covers, but is not limited to, monoclonal antibodies (including full length monoclonal antibodies), polyclonal antibodies, multi-specific antibodies (e.g., bispecific antibodies), caninized antibodies, fully canine antibodies, chimeric antibodies and camelized single domain antibodies. "Parental antibodies" are antibodies obtained by exposure of an immune system to an antigen prior to modification of the antibodies for an intended use, such as caninization of an antibody for use as a canine therapeutic antibody.

As used herein, antibodies of the present invention that "block" or is "blocking" or is "blocking the binding" of e.g., a canine receptor to its binding partner (ligand), is an antibody that blocks (partially or fully) the binding of the canine receptor to its canine ligand and vice versa, as determined in standard binding assays (e.g., BIACore®, ELISA, or flow cytometry).

Typically, an antibody or antigen binding fragment of the invention retains at least 10% of its canine antigen binding activity (when compared to the parental antibody) when that activity is expressed on a molar basis. Preferably, an antibody or antigen binding fragment of the invention retains at least 20%, 50%, 70%, 80%, 90%, 95% or 100% or more of the canine antigen binding affinity as the parental antibody. It is also intended that an antibody or antigen binding fragment of the invention can include conservative or non-conservative amino acid substitutions (referred to as "conservative variants" or "function conserved variants" of the antibody) that do not substantially alter its biologic activity.

"Isolated antibody" refers to the purification status and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

As used herein, a "chimeric antibody" is an antibody having the variable domain from a first antibody and the constant domain from a second antibody, where the first and second antibodies are from different species. [U.S. Pat. No. 4,816,567; and Morrison et al., *Proc. Natl. Acad. Sci. USA* 81: 6851-6855 (1984)]. Typically, the variable domains are obtained from an antibody from an experimental animal (the "parental antibody"), such as a rodent, and the constant domain sequences are obtained from the animal subject antibodies, e.g., human or canine so that the resulting chimeric antibody will be less likely to elicit an adverse immune response in a human or canine subject respectively, than the parental (e.g., rodent) antibody.

As used herein, the term "caninized antibody" refers to forms of antibodies that contain sequences from both canine and non-canine (e.g., murine) antibodies. In general, the caninized antibody will comprise substantially all of at least one or more typically, two variable domains in which all or substantially all of the hypervariable loops correspond to those of a non-canine immunoglobulin (e.g., comprising 6 CDRs as exemplified below), and all or substantially all of the framework (FR) regions (and typically all or substantially all of the remaining frame) are those of a canine immunoglobulin sequence. As exemplified herein, a caninized antibody comprises both the three heavy chain CDRs and the three light chain CDRS from a murine anti-canine antigen antibody together with a canine frame or a modified canine frame. A modified canine frame comprises one or more amino acids changes as exemplified herein that further optimize the effectiveness of the caninized antibody, e.g., to increase its binding to its canine antigen and/or its ability to block the binding of that canine antigen to the canine antigen's natural binding partner.

The variable regions of each light/heavy chain pair form the antibody binding site. Thus, in general, an intact antibody has two binding sites. Except in bifunctional or bispecific antibodies, the two binding sites are, in general, the same. Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5th ed.; NIH Publ. No. 91-3242 (1991); Kabat, *Adv. Prot. Chem.* 32:1-75 (1978); Kabat, et al., *J. Biol. Chem.* 252:6609-6616 (1977); Chothia, et al., *J. Mol. Biol.* 196:901-917 (1987) or Chothia, et al., *Nature* 342:878-883 (1989)].

As used herein, the term "hypervariable region" refers to the amino acid residues of an antibody that are responsible for antigen-binding. The hypervariable region comprises amino acid residues from a "complementarity determining region" or "CDR" (i.e. LCDR1, LCDR2 and LCDR3 in the light chain variable domain and HCDR1, HCDR2 and HCDR3 in the heavy chain variable domain). [See Kabat et al. *Sequences of Proteins of Immunological Interest,* 5th Ed. Public Health Service, National Institutes of Health, Bethesda, Md. (1991), defining the CDR regions of an antibody by sequence; see also Chothia and Lesk, *J. Mol. Biol.* 196: 901-917 (1987) defining the CDR regions of an antibody by structure]. As used herein, the term "framework" or "FR" residues refers to those variable domain residues other than the hypervariable region residues defined herein as CDR residues.

There are four known IgG heavy chain subtypes of dog IgG and they are referred to as IgG-A, IgG-B, IgG-C, and IgG-D. The two known light chain subtypes are referred to as lambda and kappa. In specific embodiments of the invention, besides binding and activating of canine immune cells, a canine or caninized antibody against its antigen of the present invention optimally has two attributes:

1. Lack of effector functions such as antibody-dependent cytotoxicity (ADCC) and complement-dependent cytotoxicity (CDC), and
2. be readily purified on a large scale using industry standard technologies such as that based on protein A chromatography.

None of the naturally occurring canine IgG isotypes satisfy both criteria. For example, IgG-B can be purified using protein A, but has high level of ADCC activity. On the other hand, IgG-A binds weakly to protein A, but also displays ADCC activity. Moreover, neither IgG-C nor IgG-D can be purified on protein A columns, although IgG-D displays no ADCC activity. (IgG-C has considerable ADCC activity). One way the present invention addresses these issues is by providing modified canine IgG-B antibodies of the present invention specific to an antigen of the present invention that lack the effector functions such as ADCC and can be easily purified using industry standard protein A chromatography.

As used herein an "anti-inflammatory antibody" is an antibody that can act as an anti-inflammatory agent in an animal, including a mammal such as a human, a canine, and/or a feline, particularly with respect to atopic dermatitis. In particular embodiments, the anti-inflammatory antibody binds to specific proteins in the IL-4/IL-13 signaling pathway, such as IL-4 or the receptor IL-$4R_{\alpha}$. The binding of the anti-inflammatory antibody to its corresponding antigen (e.g., IL-4 or IL-$4R_{\alpha}$) inhibits the binding of e.g., IL-4 with IL-$4R_{\alpha}$, and interferes with and/or prevents the signaling of this pathway, thereby interfering with or preventing the chronic inflammation associated with atopic dermatitis.

"Homology", as used herein, refers to sequence similarity between two polynucleotide sequences or between two polypeptide sequences when they are optimally aligned. When a position in both of the two compared sequences is occupied by the same base or amino acid residue, e.g., if a position in each of two DNA molecules is occupied by adenine, then the molecules are homologous at that position. The percent of homology is the number of homologous positions shared by the two sequences divided by the total number of positions compared×100. For example, if 6 of 10 of the positions in two sequences are matched or homologous when the sequences are optimally aligned then the two sequences are 60% homologous. Generally, the comparison is made when two sequences are aligned to give maximum percent homology. Sequence identity refers to the degree to which the amino acids of two polypeptides are the same at equivalent positions when the two sequences are optimally aligned.

As used herein one amino acid sequence is 100% "identical" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In particular embodiments, selected deletions or insertions that could otherwise alter the correspondence between the two amino acid sequences are taken into account. Sequence similarity includes identical residues and nonidentical, biochemically related amino acids. Biochemically related amino acids that share similar properties and may be interchangeable.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity [see, e.g., Watson et al., *Molecular Biology of the Gene*, The Benjamin/Cummings Pub. Co., p. 224 (4th Ed.; 1987)]. In addition, substitutions of structurally or functionally similar amino acids are less likely to disrupt biological activity. Exemplary conservative substitutions are set forth in Table A directly below.

TABLE A

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |

TABLE A-continued

Exemplary Conservative Amino Acid Substitutions

| Original residue | Conservative substitution |
|---|---|
| Phe (F) | Tyr; Met; Leu |
| Pro (P) | Ala; Gly |
| Ser (S) | Thr |
| Thr (T) | Ser |
| Trp (W) | Tyr; Phe |
| Tyr (Y) | Trp; Phe |
| Val (V) | Ile; Leu |

Function-conservative variants of the antibodies of the invention are also contemplated by the present invention. "Function-conservative variants," as used herein, refers to antibodies or fragments in which one or more amino acid residues have been changed without altering a desired property, such an antigen affinity and/or specificity. Such variants include, but are not limited to, replacement of an amino acid with one having similar properties, such as the conservative amino acid substitutions of Table A above.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The present invention provides isolated caninized antibodies of the present invention, methods of use of the antibodies in the treatment of a condition e.g., the treatment of atopic dermatitis in canines. In canine, there are four IgG heavy chains referred to as A, B, C, and D. These heavy chains represent four different subclasses of dog IgG, which are referred to as IgG-A (or IgGA), IgG-B (or IgGB), IgG-C (or IgGC) and IgG-D (or IgGD). Each of the two heavy chains consists of one variable domain (VH) and three constant domains referred to as CH-1, CH-2, and CH-3. The CH-1 domain is connected to the CH-2 domain via an amino acid sequence referred to as the "hinge" or alternatively as the "hinge region".

The nucleic acid and amino acid sequences of these four heavy chains were first identified by Tang et al. [Vet. Immunol. Immunopathol. 80: 259-270 (2001)]. The amino acid and nucleic sequences for these heavy chains are also available from the GenBank data bases. For example, the amino acid sequence of IgGA heavy chain has accession number AAL35301.1, IgGB has accession number AAL35302.1, IgGC has accession number AAL35303.1, and IgGD has accession number (AAL35304.1). Canine antibodies also contain two types of light chains, kappa and lambda. The DNA and amino acid sequence of these light chains can be obtained from GenBank Databases. For example, the kappa light chain amino acid sequence has accession number ABY 57289.1 and the lambda light chain has accession number ABY 55569.1.

In the present invention, the amino acid sequence for each of the four canine IgG Fc fragments is based on the identified boundary of CH1 and CH2 domains as determined by Tang et al, supra. Caninized murine anti-canine antibodies that bind canine IL-4$R_\alpha$ include, but are not limited to: antibodies of the present invention that comprise canine IgG-A, IgG-B, IgG-C, and IgG-D heavy chains and/or canine kappa or lambda light chains together with murine anti-canine IL-41$t_\alpha$ CDRs. Accordingly, the present invention provides isolated caninized murine anti-canine antibodies of the present invention that bind to canine IL-4$R_\alpha$ and block the binding of that canine IL-41$t_\alpha$ to their natural binding partners canine IL-4 and/or canine IL-13.

Accordingly, the present invention further provides caninized murine antibodies and methods of use of the antibodies of the present invention in the treatment of a condition e.g., the treatment of atopic dermatitis in canines.

The present invention further provides full length canine heavy chains that can be matched with corresponding light chains to make a caninized antibody. Accordingly, the present invention further provides caninized murine anti-canine antigen antibodies (including isolated caninized murine anti-canine antibodies) of the present invention and methods of use of the antibodies of the present invention in the treatment of a condition e.g., the treatment of atopic dermatitis in canines.

The present invention also provides antibodies of the present invention that comprise a canine fragment crystallizable region (cFc region) in which the cFc has been genetically modified to augment, decrease, or eliminate one or more effector functions. In one aspect of the present invention, the genetically modified cFc decreases or eliminates one or more effector functions. In another aspect of the invention the genetically modified cFc augments one or more effector function. In certain embodiments, the genetically modified cFc region is a genetically modified canine IgGB Fc region. In another such embodiment, the genetically modified cFc region is a genetically modified canine IgGC Fc region. In a particular embodiment the effector function is antibody-dependent cytotoxicity (ADCC) that is augmented, decreased, or eliminated. In another embodiment the effector function is complement-dependent cytotoxicity (CDC) that is augmented, decreased, or eliminated. In yet another embodiment, the cFc region has been genetically modified to augment, decrease, or eliminate both the ADCC and the CDC.

In order to generate variants of canine IgG that lack effector functions, a number of mutant canine IgGB heavy chains were generated. These variants may include one or more of the following single or combined substitutions in the Fc portion of the heavy chain amino acid sequence: P4A, D31A, N63A, G64P, T65A, A93G, and P95A. Variant heavy chains (i.e., containing such amino acid substitutions) were cloned into expression plasmids and transfected into HEK 293 cells along with a plasmid containing the gene encoding a light chain. Intact antibodies expressed and purified from HEK 293 cells were evaluated for binding to $Fc_\gamma RI$ and C1q to assess their potential for mediation of immune effector functions. [See, U.S. Pat. No. 10,106,607 B2, the contents of which are hereby incorporated by reference in its entirety.]

The present invention also provides modified canine IgG-Ds which in place of its natural IgG-D hinge region they comprise a hinge region from:

```
IgG-A:
                                    SEQ ID NO: 6
FNECRCTDTPPCPVPEP

IgG-B:
                                    SEQ ID NO: 7
PKRENGRVPRPPDCPKCPAPEM;
or

IgG-C:
                                    SEQ ID NO: 8
AKECECKCNCNNCPCPGCGL.
```

Alternatively, the IgG-D hinge region can be genetically modified by replacing a serine residue with a proline residue, i.e., PKESTCKCIPPCPVPES, SEQ ID NO: 9 (with the proline residue (P) underlined and in bold substituting for the naturally occurring serine residue). Such modifications can lead to a canine IgG-D lacking fab arm exchange. The modified canine IgG-Ds can be constructed using standard methods of recombinant DNA technology [e.g., Maniatis et al., *Molecular Cloning, A Laboratory Manual* (1982)]. In order to construct these variants, the nucleic acids encoding the amino acid sequence of canine IgG-D can be modified so that it encodes the modified IgG-Ds. The modified nucleic acid sequences are then cloned into expression plasmids for protein expression.

The six complementary determining regions (CDRs) of a caninized murine anti-canine antibody, as described herein can comprises a canine antibody kappa light chain comprising a murine light chain LCDR1, LCDR2, and LCDR3 and a canine antibody heavy chain IgG comprising a murine heavy chain HCDR1, HCDR2, and HCDR3.

Nucleic Acids

The present invention further comprises the nucleic acids encoding the antibodies of the present invention (see e.g., Examples below).

Also included in the present invention are nucleic acids that encode immunoglobulin polypeptides comprising amino acid sequences that are at least about 70% identical, preferably at least about 80% identical, more preferably at least about 90% identical and most preferably at least about 95% identical (e.g., 95%, 96%, 97%, 98%, 99%, 100%) to the amino acid sequences of the caninized antibodies, with the exception of the CDRs which do not change, provided herein when the comparison is performed by a BLAST algorithm wherein the parameters of the algorithm are selected to give the largest match between the respective sequences over the entire length of the respective reference sequences. The present invention further provides nucleic acids that encode immunoglobulin polypeptides comprising amino acid sequences that are at least about 70% similar, preferably at least about 80% similar, more preferably at least about 90% similar and most preferably at least about 95% similar (e.g., 95%, 96%, 97%, 98%, 99%, 100%) to any of the reference amino acid sequences when the comparison is performed with a BLAST algorithm, wherein the parameters of the algorithm are selected to give the largest match between the respective sequences over the entire length of the respective reference sequences, are also included in the present invention.

As used herein, nucleotide and amino acid sequence percent identity can be determined using C, MacVector (MacVector, Inc. Cary, N.C. 27519), Vector NTI (Informax, Inc. MD), Oxford Molecular Group PLC (1996) and the Clustal W algorithm with the alignment default parameters,

15

16 and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wis.) pileup program using the default parameters.

The following references relate to BLAST algorithms often used for sequence analysis: BLAST ALGORITHMS: Altschul, S. F., et al., *J. Mol. Biol.* 215:403-410 (1990); Gish, W., et al., *Nature Genet.* 3:266-272 (1993); Madden, T. L., et al., *Meth. Enzymol.* 266:131-141(1996); Altschul, S. F., et al., *Nucleic Acids Res.* 25:3389-3402 (1997); Zhang, J., et al., *Genome Res.* 7:649-656 (1997); Wootton, J. C., et al., *Comput. Chem.* 17:149-163 (1993); Hancock, J. M. et al., *Comput. Appl. Biosci.* 10:67-70 (1994); ALIGNMENT SCORING SYSTEMS: Dayhoff, M. O., et al., "A model of evolutionary change in proteins." in *Atlas of Protein Sequence and Structure*, vol. 5, suppl. 3. M. O. Dayhoff (ed.), pp. 345-352, (1978); *Natl. Biomed. Res. Found.*, Washington, D.C.; Schwartz, R. M., et al., "Matrices for detecting distant relationships." in Atlas of Protein Sequence and Structure, vol. 5, suppl. 3." (1978), M. O. Dayhoff (ed.), pp. 353-358 (1978), *Natl. Biomed. Res. Found.*, Washington, D.C.; Altschul, S. F., *J. Mol. Biol.* 219:555-565 (1991); States, D. J., et al., *Methods* 3:66-70(1991); Henikoff, S., et al., *Proc. Natl. Acad Sci. USA* 89:10915-10919 (1992); Altschul, S. F., et al., *J. Mol. Evol.* 36:290-300 (1993); ALIGNMENT STATISTICS: Karlin, S., et al., *Proc. Natl. Acad. Sci. USA* 87:2264-2268 (1990); Karlin, S., et al., *Proc. Natl. Acad. Sci. USA* 90:5873-5877 (1993); Dembo, A., et al., *Ann. Prob.* 22:2022-2039 (1994); and Altschul, S. F. "Evaluating the statistical significance of multiple distinct local alignments." in *Theoretical and Computational Methods in Genome Research* (S. Suhai, ed.), pp. 1-14, Plenum, N.Y. (1997).

Antibodies of the present invention can be produced recombinantly by methods that are known in the field. Mammalian cell lines available as hosts for expression of the antibodies or fragments disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or anti-gen-binding portion or fragment thereof, the light chain and/or antigen-binding fragment thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies can be recovered from the culture medium using standard protein purification methods. Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

In general, glycoproteins produced in a particular cell line or transgenic animal will have a glycosylation pattern that is characteristic for glycoproteins produced in the cell line or transgenic animal. Therefore, the particular glycosylation pattern of an antibody will depend on the particular cell line or transgenic animal used to produce the antibody. However, all antibodies encoded by the nucleic acid molecules provided herein, or comprising the amino acid sequences provided herein, comprise the instant invention, independent of the glycosylation pattern that the antibodies may have. Similarly, in particular embodiments, antibodies with a glycosylation pattern comprising only non-fucosylated N-glycans may be advantageous, because these antibodies have been shown to typically exhibit more potent efficacy than their fucosylated counterparts both in vitro and in vivo [See for example, Shinkawa et al., *J. Biol. Chem.* 278: 3466-3473 (2003); U.S. Pat. Nos. 6,946,292 and 7,214,775].

Canine IL-4 Receptor Alpha Receptor

The cDNA encoding a predicted full length canine IL-4 receptor alpha chain (SEQ ID NO: 1) was identified through a search of the Genbank database (accession #XM_547077.4; see also, U.S. Pat. No. 7,208,579 B2). This predicted cDNA encodes 823 amino acids (SEQ ID NO: 2) including a 25 amino acid leader sequence and is identified as accession #XP_547077.3. The mature predicted canine IL-4 receptor α chain protein (SEQ ID NO: 4) shares 65% identity with human IL-4 receptor α chain (accession #NP_000409.1) and 70% identity with swine IL-4 receptor α chain (accession #NP_999505.1). The mature predicted canine IL-4 receptor α chain protein is encoded by the nucleotide sequence identified as SEQ ID NO: 3. Comparison of the predicted mature IL-4 receptor α chain with the known sequences of human IL-4 receptor α chain identified the extracellular domain (ECD) of the mature canine IL-4 receptor α chain protein and is designated as SEQ ID NO: 5. This has all been previously described in [US2018/0346580; hereby incorporated herein in its entirety].

Canine IL-4 receptor α chain full length DNA with signal sequence

[SEQ ID NO: 1]

atgggcagactgtgcagcggcctgaccttccccgtgagctgcctggtgctggtgtgggtggccagcagcggcagcgt gaaggtgctgcacgagcccagctgcttcagcgactacatcagcaccagcgtgtgccagtggaagatggaccacccca ccaactgcagcgccgagctgagactgagctaccagctggacttcatgggcagcgagaaccacacctgcgtgcccgag aacagagaggacagcgtgtgcgtgtgcagcatgcccatcgacgacgccgtggaggccgacgtgtaccagctggacct gtgggccggccagcagctgctgtggagcggcagcttccagcccagcaagcacgtgaagcccagaacccccggcaacc -continued tgaccgtgcaccccaacatcagccacacctggctgctgatgtggaccaacccctaccccaccgagaaccacctgcac agcgagctgacctacatggtgaacgtgagcaacgacaacgaccccgaggacttcaaggtgtacaacgtgacctacat gggccccaccctgagactggccgccagcaccctgaagagcggcgccagctacagcgccagagtgagagcctgggccc agacctacaacagcacctggagcgactggagccccagcaccacctggctgaactactacgagccctgggagcagcac ctgcccctgggcgtgagcatcagctgcctggtgatcctggccatctgcctgagctgctacttcagcatcatcaagat caagaagggctggtgggaccagatccccaaccccgcccacagcccccctggtggccatcgtgatccaggacagccagg tgagcctgtggggcaagagaagcagaggccaggagcccgccaagtgcccccactggaagacctgcctgaccaagctg ctgccctgcctgctggagcacggcctgggcagagaggaggagagccccaagaccgccaagaacggcccccctgcaggg ccccggcaagcccgcctggtgccccgtggaggtgagcaagaccatcctgtggcccgagagcatcagcgtggtgcagt gcgtggagctgagcgaggcccccgtggacaacgaggaggaggaggaggtggaggaggacaagagaagcctgtgcccc agcctggagggcagcggcggcagcttccaggagggcagagagggcatcgtggccagactgaccgagagcctgttcct ggacctgctgggcggcgagaacggcggcttctgcccccagggcctggaggagagctgcctgcccccccccagcggca gcgtgggcgcccagatgccctgggcccagttccccagagccggccccagagccgcccccgagggccccgagcagccc agaagacccgagagcgccctgcaggccagccccacccagagcgccggcagcagcgccttccccgagcccccccccgt ggtgaccgacaaccccgcctacagaagcttcggcagcttcctgggccagagcagcgaccccggcgacggcgacagcg accccgagctggccgacagacccggcgaggccgaccccggcatccccagcgcccccagcccccccgagcccccccgcc gccctgcagcccgagcccgagagctgggagcagatcctgagacagagcgtgetgcagcacagagccgcccccgcccc cggccccggccccggcagcggctacagagagttcacctgcgccgtgaagcagggcagcgcccccgacgccggcggcc ccggcttcggccccagcggcgaggccggctacaaggccttctgcagcctgctgcccggcggcgccacctgccccggc accagcggcggcgaggccggcagcggcgagggcggctacaagcccttccagagcctgacccccggctgccccggcgc ccccacccccgtgcccgtgcccctgttcaccttcggcctggacaccgagcccccggcagcccccaggacagcctgg gcgccggcagcagccccgagcacctgggcgtggagcccgccggcaaggaggaggacagcagaaagaccctgctggcc cccgagcaggccaccgacccccctgagagacgacctggccagcagcatcgtgtacagcgccctgacctgccacctgtg cggccacctgaagcagtggcacgaccaggaggagagaggcaaggcccacatcgtgcccagcccctgctgcggctgct gctgcggcgacagaagcagcctgctgctgagccccctgagagcccccaacgtgctgcccggcggcgtgctgctggag gccagcctgagccccgccagcctggtgcccagcggcgtgagcaaggagggcaagagcagccccttcagccagcccgc cagcagcagcgcccagagcagcagccagacccccaagaagctggccgtgctgagcaccgagcccacctgcatgagcg ccagc Canine IL-4 receptor α full length protein with signal sequence in bold font
[SEQ ID NO: 2]

MGRLCSGLTFPVSCLVLVWVASSGSVKVLHEPSCFSDYISTSVCQWKMDHPTNCSAELRLSYQLDFMGSENHTCVPE

NREDSVCVCSMPIDDAVEADVYQLDLWAGQQLLWSGSFQPSKHVKPRTPGNLTVHPNISHTWLLMWTNPYPTENHLH

SELTYMVNVSNDNDPEDFKVYNVTYMGPTLRLAASTLKSGASYSARVRAWAQTYNSTWSDWSPSTTWLNYYEPWEQH

LPLGVSISCLVILAICLSCYFSIIKIKKGWWDQIPNPAHSPLVAIVIQDSQVSLWGKRSRGQEPAKCPHWKTCLTKL

LPCLLEHGLGREEESPKTAKNGPLQGPGKPAWCPVEVSKTILWPESISVVQCVELSEAPVDNEEEEEVEEDKRSLCP

SLEGSGGSFQEGREGIVARLTESLFLDLLGGENGGFCPQGLEESCLPPPSGSVGAQMPWAQFPRAGPRAAPEGPEQP

RRPESALQASPTQSAGSSAFPEPPPVVTDNPAYRSFGSFLGQSSDPGDGDSDPELADRPGEADPGIPSAPQPPEPPA

ALQPEPESWEQILRQSVLQHRAAPAPGPGPGSGYREFTCAVKQGSAPDAGGPGFGPSGEAGYKAFCSLLPGGATCPG

TSGGEAGSGEGGYKPFQSLTPGCPGAPTPVPVPLFTFGLDTEPPGSPQDSLGAGSSPEHLGVEPAGKEEDSRKTLLA

PEQATDPLRDDLASSIVYSALTCHLCGHLKQWHDQEERGKAHIVPSPCCGCCCGDRSSLLLSPLRAPNVLPGGVLLE

ASLSPASLVPSGVSKEGKSSPFSQPASSSAQSSSQTPKKLAVLSTEPTCMSAS

-continued

Canine IL-4 receptor α mature full length protein without signal sequence
[SEQ ID NO: 4]

VKVLHEPSCFSDYISTSVCQWKMDHPTNCSAELRLSYQLDFMGSENHTCVPENREDSVCVCSMPIDDAVEADVYQLD

LWAGQQLLWSGSFQPSKHVKPRTPGNLTVHPNISHTWLLMWTNPYPTENHLHSELTYMVNVSNDNDPEDFKVYNVTY

MGPTLRLAASTLKSGASYSARVRAWAQTYNSTWSDWSPSTTWLNYYEPWEQHLPLGVSISCLVILAICLSCYFSIIK

IKKGWWDQIPNPAHSPLVAIVIQDSQVSLWGKRSRGQEPAKCPHWKTCLTKLLPCLLEHGLGREEESPKTAKNGPLQ

GPGKPAWCPVEVSKTILWPESISVVQCVELSEAPVDNEEEEEVEEDKRSLCPSLEGSGGSFQEGREGIVARLTESLF

LDLLGGENGGFCPQGLEESCLPPPSGSVGAQMPWAQFPRAGPRAAPEGPEQPRRPESALQASPTQSAGSSAFPEPPP

VVTDNPAYRSFGSFLGQSSDPGDGDSDPELADRPGEADPGIPSAPQPPEPPAALQPEPESWEQILRQSVLQHRAAPA

PGPGPGSGYREFTCAVKQGSAPDAGGPGFGPSGEAGYKAFCSLLPGGATCPGTSGGEAGSGEGGYKPFQSLTPGCPG

APTPVPVPLFTFGLDTEPPGSPQDSLGAGSSPEHLGVEPAGKEEDSRKTLLAPEQATDPLRDDLASSIVYSALTCHL

CGHLKQWHDQEERGKAHIVPSPCCGCCCGDRSSLLLSPLRAPNVLPGGVLLEASLSPASLVPSGVSKEGKSSPFSQP

ASSSAQSSSQTPKKLAVLSTEPTCMSAS

Canine IL-4 receptor α mature full length DNA without signal sequence
[SEQ ID NO: 3]

gtgaaggtgctgcacgagcccagctgcttcagcgactacatcagcaccagcgtgtgccagtggaagatggaccaccc caccaactgcagcgccgagctgagactgagctaccagctggacttcatgggcagcgagaaccacacctgcgtgcccg agaacagagaggacagcgtgtgcgtgtgcagcatgcccatcgacgacgccgtggaggccgacgtgtaccagctggac ctgtgggccggccagcagctgctgtggagcggcagcttccagcccagcaagcacgtgaagcccagaacccccggcaa cctgaccgtgcaccccaacatcagccacacctggctgctgatgtggaccaacccctaccccaccgagaaccacctgc acagcgagctgacctacatggtgaacgtgagcaacgacaacgaccccgaggacttcaaggtgtacaacgtgacctac atgggccccaccctgagactggccgccagcaccctgaagagcggcgccagctacagcgccagagtgagagcctgggc ccagacctacaacagcacctggagcgactggagccccagcaccacctggctgaactactacgagccctgggagcagc acctgcccctgggcgtgagcatcagctgcctggtgatcctggccatctgcctgagctgctacttcagcatcatcaag atcaagaagggctggtgggaccagatccccaaccccgcccacagcccccctggtggccatcgtgatccaggacagcca ggtgagcctgtggggcaagagaagcagaggccaggagcccgccaagtgcccccactggaagacctgcctgaccaagc tgctgccctgcctgctggagcacggcctgggcagagaggaggagagccccaagaccgccaagaacggcccctgcag ggccccggcaagcccgcctggtgccccgtggaggtgagcaagaccatcctgtggcccgagagcatcagcgtggtgca gtgcgtggagctgagcgaggcccccgtggacaacgaggaggaggaggaggtggaggaggacaagagaagcctgtgcc ccagcctggagggcagcggcggcagcttccaggagggcagagagggcatcgtggccagactgaccgagagcctgttc ctggacctgctgggcggcgagaacggcggcttctgcccccagggcctggaggagagctgcctgcccccccccagcgg cagcgtgggcgcccagatgccctgggcccagttccccagagccggccccagagccgcccccgagggccccgagcagc ccagaagacccgagagcgccctgcaggccagccccacccagagcgccggcagcagcgccttccccgagccccccccc gtggtgaccgacaaccccgcctacagaagcttcggcagcttcctgggccagagcagcgaccccggcgacggcgacag cgaccccgagctggccgacagacccggcgaggccgaccccggcatccccagcgcccccagcccccccgagcccccccg ccgccctgcagcccgagcccgagagctgggagcagatcctgagacagagcgtgetgcagcacagagccgcccccgcc cccggccccggccccggcagcggctacagagagttcacctgcgccgtgaagcagggcagcgcccccgacgccggcgg ccccggcttcggccccagcggcgaggccggctacaaggccttctgcagcctgctgcccggcggcgccacctgccccg gcaccagcggcggcgaggccggcagcggcgagggcggctacaagcccttccagagcctgacccccggctgccccggc gcccccacccccgtgcccgtgcccctgttcaccttcggcctggacaccgagcccccggcagcccccaggacagcct gggcgccggcagcagccccgagcacctgggcgtggagcccgccggcaaggaggaggacagcagaaagaccctgctgg cccccgagcaggccaccgacccccctgagagacgacctggccagcagcatcgtgtacagcgccctgacctgccacctg tgcggccacctgaagcagtggcacgaccaggaggagagaggcaaggcccacatcgtgcccagcccctgctgcggctg -continued ctgctgcggcgacagaagcagcctgctgctgagccccctgagagcccccaacgtgctgcccggcggcgtgctgctgg aggccagcctgagccccgccagcctggtgcccagcggcgtgagcaaggagggcaagagcagccccttcagccagccc gccagcagcagcgcccagagcagcagccagacccccaagaagctggccgtgctgagcaccgagcccacctgcatgag cgccagc Canine IL-4 receptor α chain extracellular domain

[SEQ ID NO: 5]

VKVLHEPSCFSDYISTSVCQWKMDHPTNCSAELRLSYQLDFMGSENHTCVPENREDSVCVCSMPIDDAVEADVYQLD

LWAGQQLLWSGSFQPSKHVKPRTPGNLTVHPNISHTWLLMWTNPYPTENHLHSELTYMVNVSNDNDPEDFKVYNVTY

MGPTLRLAASTLKSGASYSARVRAWAQTYNSTWSDWSPSTTWLNYYEPWEQHLP

Antibody Protein Engineering

By way of example, and not limitation, the canine heavy chain constant region can be from IgG-B or a modified cFc, such as the IgG-Bm used herein [see, U.S. Pat. No. 10,106,607 B2, hereby incorporated by reference in its entirety] and the canine light chain constant region can be from kappa.

The antibodies can be engineered to include modifications to the canine framework and/or the canine frame residues within the variable domains of a parental (i.e., mouse) monoclonal antibody, e.g. to improve the properties of the antibody.

Pharmaceutical Compositions and Administration

To prepare pharmaceutical or sterile compositions comprising the antibodies of the present invention, these antibodies can be admixed with a pharmaceutically acceptable carrier or excipient. [See, e.g., *Remington's Pharmaceutical Sciences and U.S. Pharmacopeia: National Formulary*, Mack Publishing Company, Easton, Pa. (1984)].

Formulations of therapeutic and diagnostic agents may be prepared by mixing with acceptable carriers, excipients, or stabilizers in the form of, e.g., lyophilized powders, slurries, aqueous solutions or suspensions [see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.]. In one embodiment, the antibodies of the present invention are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antibody compositions, administered alone or in combination with another agent, can be determined by standard pharmaceutical procedures in cell cultures or experimental animals, e.g., for determining the $LD_{50}$ (the dose lethal to 50% of the population) and the ED50 (the dose therapeutically effective in 50% of the population). The dose ratio between toxic and therapeutic effects is the therapeutic index ($LD_{50}/ED_{50}$). In particular aspects, antibodies exhibiting high therapeutic indices are desirable. The data obtained from these cell culture assays and animal studies can be used in formulating a range of dosage for use in canines. The dosage of such compounds lies preferably within a range of circulating concentrations that include the ED50 with little or no toxicity. The dosage may vary within this range depending upon the dosage form employed and the route of administration.

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial. In particular embodiments, the antibodies of the present invention can be administered by an invasive route such as by injection. In further embodiments of the invention, the antibodies of the present invention, or pharmaceutical composition thereof, is administered intravenously, subcutaneously, intramuscularly, intraarterially, or by inhalation, aerosol delivery. Administration by non-invasive routes (e.g., orally; for example, in a pill, capsule or tablet) is also within the scope of the present invention.

Compositions can be administered with medical devices known in the art. For example, a pharmaceutical composition of the invention can be administered by injection with a hypodermic needle, including, e.g., a prefilled syringe or autoinjector. The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

The pharmaceutical compositions disclosed herein may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternatively, one may administer the antibodies of the present invention in a local rather than systemic manner, often in a depot or sustained release formulation.

The administration regimen depends on several factors, including the serum or tissue turnover rate of the therapeutic antibodies, the level of symptoms, the immunogenicity of the therapeutic antibodies and the accessibility of the target cells in the biological matrix. Preferably, the administration regimen delivers sufficient therapeutic antibodies to effect improvement in the target disease/condition state, while simultaneously minimizing undesired side effects. Accordingly, the amount of biologic delivered depends in part on the particular therapeutic antibodies and the severity of the condition being treated. Guidance in selecting appropriate doses of therapeutic antibodies is available [see, e.g., Wawrzynczak *Antibody Therapy*, Bios Scientific Pub. Ltd, Oxfordshire, U K (1996); Kresina (ed.) *Monoclonal Antibodies, Cytokines and Arthritis*, Marcel Dekker, New York, N.Y. (1991); Bach (ed.) *Monoclonal Antibodies and Peptide Therapy in Autoimmune Diseases*, Marcel Dekker, New York, N.Y. (1993); Baert, et al. *New Engl. J Med* 348:601-608 (2003); Milgrom et al. *New Engl. J Med.* 341:1966-1973 (1999); Slamon et al. *New Engl. J Med* 344:783-792 (2001); Beniaminovitz et al. *New Engl. Med.* 342:613-619 (2000); Ghosh et al. *New Engl. J. Med.* 348:24-32 (2003); Lipsky et al. *New Engl. J. Med.* 343:1594-1602 (2000)].

Determination of the appropriate dose is made by the veterinarian, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of the symptoms.

Antibodies provided herein may be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 μg/kg body weight, more generally at least 0.2 μg/kg, 0.5 μg/kg, 1 μg/kg, 10 μg/kg, 100 μg/kg, 0.25 mg/kg, 1.0 mg/kg, 2.0 mg/kg, 5.0 mg/ml, 10 mg/kg, 25 mg/kg, 50 mg/kg or more [see, e.g., Yang, et al. *New Engl. J. Med.* 349:427-434 (2003); Herold, et al. *New Engl. J. Med* 346:1692-1698 (2002); Liu, et al. *J. Neurol. Neurosurg. Psych.* 67:451-456 (1999); Portielji, et al. *Cancer Immunol. Immunother.* 52:133-144 (2003)]. Doses may also be provided to achieve a pre-determined target concentration of antibodies of the present invention in the canine's serum, such as 0.1, 0.3, 1, 3, 10, 30, 100, 300 μg/ml or more. In other embodiments, antibodies of the present invention is administered subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject (e.g., a canine) with a disorder, condition and/or symptom, or with the potential to develop such a disorder, disease or symptom.

As used herein, the terms "therapeutically effective amount", "therapeutically effective dose" and "effective amount" refer to an amount of antibodies of the present invention that, when administered alone or in combination with an additional therapeutic agent to a cell, tissue, or subject, e.g., canine, is effective to cause a measurable improvement in one or more symptoms of a disease or condition or the progression of such disease or condition. A therapeutically effective dose further refers to that amount of the antibodies sufficient to result in at least partial amelioration of symptoms, e.g., treatment, healing, prevention or amelioration of the relevant medical condition, or an increase in rate of treatment, healing, prevention or amelioration of such conditions. When applied to a combination, a therapeutically effective dose refers to combined amounts of the active ingredients that result in the therapeutic effect, whether administered in combination, serially, or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess severity of the condition.

EXAMPLES

Example 1

Anti-IL-4 Receptor Alpha Antibodies

General Material and Methods

The recombinant proteins were obtained by providing the amino acid sequence for a selected protein to a commercial manufacturer (ATUM, Newark, Calif.), who in turn chose an appropriate nucleotide sequence that encoded this amino acid sequence. The nucleotide sequences can also be obtained from publicly available DNA databases, such as GenBank®. The commercial manufacturer then chemically synthesized the nucleic acid, which next was cloned by ATUM into an expression plasmid (pD2610-v10; available from AUTM) for producing the corresponding recombinant protein. The plasmid was placed into either HEK-293 cells or CHO cells to express the recombinant protein, which was then isolated by conventional methods.

Balb/c mice were immunized multiple times (with 10 μg each time) over a 17-day period. The immunizing antigen was the canine IL-4 R alpha chain extracellular domain (ECD)-human Fc fusion protein. Following immunization, serum was collected from each mouse and tested for reactivity with canine IL-4 receptor alpha chain ECD HIS-tagged protein. The spleen cells of the mouse with the highest serum anti-IL-4 receptor alpha chain ECD titer were fused to the myeloma P3X63Ag8.653 cell line. Approximately 2 weeks following fusion, supernatant from putative hybridoma cells were tested by ELISA for their reactivity to the IL-4 receptor alpha chain ECD HIS-tagged protein. Hybridomas producing strong positive signals in the ELISA were subcloned by limiting dilution and tested again for reactivity to canine IL-4 receptor alpha chain ECD HIS-tagged protein.

Anti-canine IL-4 receptor alpha antibodies include the antibody c152H11VL3-cCLk-s/c152H11VH3-cIgG-Bm and the antibody c146E2VL3-cCLk-s/c146E2VH3-cIgG-Bm. Sets of the six (6) CDRs (three individual light chains (LC) and three heavy chains (HC) sequences) for these two antibodies are provided below in Tables 1A and 1B. Table 1A provides nucleic acids that encode the amino acid sequences of the twelve CDRs listed in Table 1B. The amino acid sequences of the full length light chains and heavy chains of these caninized antibodies are provided immediately following Table 1B below.

IL-4 R Alpha Antibody CDR Nucleic Acid and Amino Acid Sequences

TABLE 1A

| CDR | | SEQ ID NO: |
|---|---|---|
| | 146E2 | |
| HCDR1 | agatactggatgcac | 11 |
| HCDR2 | atgattcaccccgacagcggcaacatcaactacaacgag cggttcaagacc | 13 |
| HCDR3 | cagctgcggaacgccatggattat | 15 |
| LCDR1 | agagccagcgagagcgtggacagctacggcaacagcttc ctgaac | 17 |
| LCDR2 | agagccagcaacctggcctct | 19 |
| LCDR3 | cagcagaactacgagaaccccagaacc | 21 |
| | 152H11 | |
| HCDR1 | agctacggcatgagc | 23 |
| HCDR2 | acaatcagcagaggcggcgactacacctactatcccgac agcgtgaagggc | 25 |
| HCDR3 | ggcaccctgaacaaccggggctttgcttct | 27 |
| LCDR1 | aaggccagccagaacgtgggcaccaatgtggcc | 29 |
| LCDR2 | agcgccagctaccggtactct | 31 |
| LCDR3 | cagcagtacaacagctacccctacacc | 33 |

TABLE 1B

| | 146E2 | SEQ ID NO: | 152H11 | SEQ ID NO: |
|---|---|---|---|---|
| HCDR1 | RYWMH | 12 | SYGMS | 24 |
| HCDR2 | MIHPDSGNINYNERFKT | 14 | TISRGGDYTYYPDSVKG | 26 |
| HCDR3 | QLRNAMDY | 16 | GTLNNRGFAS | 28 |
| LCDR1 | RASESVDSYGNSFLN | 18 | KASQNVGTNVA | 30 |
| LCDR2 | RASNLAS | 20 | SASYRYS | 32 |
| LCDR3 | QQNYENPRT | 22 | QQYNSYPYT | 34 |

C152H11VL3-cCLk-s (kappa light chain):
[SEQ ID NO: 35]
EIVMTQSPASLSLSQEEKVTITCKASQNVGTNVAWYQQKPGQAPKLLIYSASYRYSGLPDRFSG
SGSGTDFSFTISSLEPEDVAEFFCQQYNSYPYTFGQGTKLEIKRNDAQPAVYLFQPSPDQLHTG
SASVVCLLNSFYPKDINVKWKVDGVIQDTGIQESVTEQDKDSTYSLSSTLTMSSTEYLSHELYS
CEITHKSLPSTLIKSFQRSECQRVD C152H11VH1-cIgGBm (heavy chain):
[SEQ ID NO: 36]
EVQLVESGGDLVKPGGSLRLSCAASGFTFSSYGMSWVRQAPGKGLQWVATISRGGDYTYYPDSV
KGRFTISRDNAKNTLYLQMNSLRAEDTAMYYCAKGTLNNRGFACWGQGTLVTVSSASTTAPSVF
PLAPSCGSTSGSTVALACLVSGYFPEPVTVSWNSGSLTSGVHTFPSVLQSSGLYSLSSMVTVPS
SRWPSETFTCNVAHPASKTKVDKPVPKRENGRVPRPPDCPKCPAPEMLGGPSVFIFPPKPKDTL
LIARTPEVTCVVVALDPEDPEVQISWFVDGKQMQTAKTQPREEQFAGTYRVVSVLPIGHQDWLK
GKQFTCKVNNKALPSPIERTISKARGQAHQPSVYVLPPSREELSKNTVSLTCLIKDFFPPDIDV
EWQSNGQQEPESKYRTTPPQLDEDGSYFLYSKLSVDKSRWQRGDTFICAVMHEALHNHYTQESL
SHSPG c152H11VH2-cIgGBm (heavy chain):
[SEQ ID NO: 37]
EVQLVESGGDLVKPGGSLRLSCAASGFTFSSYGMSWVRQAPDKRLQWVATISRGGDYTYYPDSV
KGRFTISRDNAKNTLYLQMNSLRAEDTAMYYCARGTLNNRGFACWGQGTLVTVSSASTTAPSVF
PLAPSCGSTSGSTVALACLVSGYFPEPVTVSWNSGSLTSGVHTFPSVLQSSGLYSLSSMVTVPS
SRWPSETFTCNVAHPASKTKVDKPVPKRENGRVPRPPDCPKCPAPEMLGGPSVFIFPPKPKDTL
LIARTPEVTCVVVALDPEDPEVQISWFVDGKQMQTAKTQPREEQFAGTYRVVSVLPIGHQDWLK -continued

GKQFTCKVNNKALPSPIERTISKARGQAHQPSVYVLPPSREELSKNTVSLTCLIKDFFPPDIDV

EWQSNGQQEPESKYRTTPPQLDEDGSYFLYSKLSVDKSRWQRGDTFICAVMHEALHNHYTQESL

SHSPG c152H11VH3-cIgG-Bm (heavy chain):

[SEQ ID NO: 38]

EVQLVESGGDLVKPGGSLRLSCAASGFTFSSYGMSWVRQAPDKRLQWVATISRGGDYTYYPDSV

KGRFTISRDNAKNTLYLQMNSLRAEDTAMYYCARGTLNNRGFASWGQGTLVTVSSASTTAPSVF

PLAPSCGSTSGSTVALACLVSGYFPEPVTVSWNSGSLTSGVHTFPSVLQSSGLYSLSSMVTVPS

SRWPSETFTCNVAHPASKTKVDKPVPKRENGRVPRPPDCPKCPAPEMLGGPSVFIFPPKPKDTL

LIARTPEVTCVVVALDPEDPEVQISWFVDGKQMQTAKTQPREEQFAGTYRVVSVLPIGHQDWLK

GKQFTCKVNNKALPSPIERTISKARGQAHQPSVYVLPPSREELSKNTVSLTCLIKDFFPPDIDV

EWQSNGQQEPESKYRTTPPQLDEDGSYFLYSKLSVDKSRWQRGDTFICAVMHEALHNHYTQESL

SHSPG c146E2VL3-cCLk-s (kappa light chain):

[SEQ ID NO: 39]

DIVLTQTPLSLSVSPGETASIYCRASESVDSYGNSFLNWYQQKPGQPPKLLIYRASNLASEIPD

RFSGSGSRTEFTLKISRVEADDAGVYYCQQNYENPRTFGQGTKLEIKRNDAQPAVYLFQPSPDQ

LHTGSASVVCLLNSFYPKDINVKWKVDGVIQDTGIQESVTEQDKDSTYSLSSTLTMSSTEYLSH

ELYSCEITHKSLPSTLIKSFQRSECQRVD c146E2VH1-cIgGBm (heavy chain):

[SEQ ID NO: 40]

EVQLVQSGAEVKKPGASVKVSCKASGYTFARYWMHWVRQAPGAGLDWMGMIHPDSGNINYNERF

KTRVTLTADTSTSTAYMELSSLRAGDIAVYYCARQLRNAMDYWGQGTLVTVSSASTTAPSVFPL

APSCGSTSGSTVALACLVSGYFPEPVTVSWNSGSLTSGVHTFPSVLQSSGLYSLSSMVTVPSSR

WPSETFTCNVAHPASKTKVDKPVPKRENGRVPRPPDCPKCPAPEMLGGPSVFIFPPKPKDTLLI

ARTPEVTCVVVALDPEDPEVQISWFVDGKQMQTAKTQPREEQFAGTYRVVSVLPIGHQDWLKGK

QFTCKVNNKALPSPIERTISKARGQAHQPSVYVLPPSREELSKNTVSLTCLIKDFFPPDIDVEW

QSNGQQEPESKYRTTPPQLDEDGSYFLYSKLSVDKSRWQRGDTFICAVMHEALHNHYTQESLSH

SPG c146E2VH2-cIgGBm (heavy chain):

[SEQ ID NO: 41]

EVQLVQSGAEVKKPGASVKVSCKASGYTFARYWMHWMKQAPGAGLDWIGMIHPDSGNINYNERF

KTKATLTADTSTSTAYMELSSLRAGDIAVYYCARQLRNAMDYWGQGTLVTVSSASTTAPSVFPL

APSCGSTSGSTVALACLVSGYFPEPVTVSWNSGSLTSGVHTFPSVLQSSGLYSLSSMVTVPSSR

WPSETFTCNVAHPASKTKVDKPVPKRENGRVPRPPDCPKCPAPEMLGGPSVFIFPPKPKDTLLI

ARTPEVTCVVVALDPEDPEVQISWFVDGKQMQTAKTQPREEQFAGTYRVVSVLPIGHQDWLKGK

QFTCKVNNKALPSPIERTISKARGQAHQPSVYVLPPSREELSKNTVSLTCLIKDFFPPDIDVEW

QSNGQQEPESKYRTTPPQLDEDGSYFLYSKLSVDKSRWQRGDTFICAVMHEALHNHYTQESLSH

SPG c146E2VH3-cIgG-Bm (heavy chain):

[SEQ ID NO: 42]

EVQLVQSGAEVKKPGASVKVSCKASGYTFARYWMHWMKQAPGAGLDWIGMIHPDSGNINYNERF

KTKATLTVDKSTSTAYMELSSLRAGDIAVYYCARQLRNAMDYWGQGTLVTVSSASTTAPSVFPL

APSCGSTSGSTVALACLVSGYFPEPVTVSWNSGSLTSGVHTFPSVLQSSGLYSLSSMVTVPSSR

WPSETFTCNVAHPASKTKVDKPVPKRENGRVPRPPDCPKCPAPEMLGGPSVFIFPPKPKDTLLI

ARTPEVTCVVVALDPEDPEVQISWFVDGKQMQTAKTQPREEQFAGTYRVVSVLPIGHQDWLKGK

-continued

```
QFTCKVNNKALPSPIERTISKARGQAHQPSVYVLPPSREELSKNTVSLTCLIKDFFPPDIDVEW

QSNGQQEPESKYRTTPPQLDEDGSYFLYSKLSVDKSRWQRGDTFICAVMHEALHNHYTQESLSH

SPG
```

In addition, the light chains for the canine IL-4 receptor alpha antibodies were also constructed with a lambda light chain as provided below.

```
C152H11LV1-cCl (lambda light chain)
                                         [SEQ ID NO: 43]
QSVLTQPASVSGSLGQRVTISCKASQNVGTNVAWYQQLPGTSPRTLIYS

ASYRYSGVPDRFSGSRSGSTATLTISGLQAEDEADYYCQQYNSYPYTFG

GGTHLTVLGQPKASPSVTLFPPSSEELGANKATLVCLISDFYPSGVTVA

WKADGSPVTQGVETTKPSKQSNNKYAASSYLSLTPDKWKSHSSFSCLVT

HEGSTVEKKVAPAECS

c146E2LV1-cCl (lambda light chain)
                                         [SEQ ID NO: 44]
QSVLTQPASVSGSLGQRVTISCRASESVDSYGNSFLNWYQQLPGKAPSL

LIYRASNLASGVPERFSGSKSGSSATLTITGLQAEDEADYYCQQNYENP

RTFGGGTHLTVLGQPKASPSVTLFPPSSEELGANKATLVCLISDFYPSG

VTVAWKADGSPVTQGVETTKPSKQSNNKYAASSYLSLTPDKWKSHSSFS

CLVTHEGSTVEKKVAPAECS
```

Example 2

STAT-6 Inhibition

Antibodies against canine IL-4 receptor alpha were tested for their ability to inhibit STAT-6 phosphorylation in DH82 Cell as follows:

Materials

1. Actively growing DH82 cells
2. DH82 Cell Growth Media (ATCC® 302003™, Eagle's Minimum Essential Medium supplied with heat-inactivated fetal bovine serum to a final concentration of 15% w/v)
3. AlphaLISA p-STAT6 (Tyr641) Assay Kit: Perkin Elmer Catalog: ALSU-PST6-A-HV
4. Recombinant canine IL-4: R&D Systems, Catalog: 752-CL/CF
5. Recombinant canine IL-13: R&D Systems, Catalog: 5894-CL/CF
6. Perkin Elmer Envision
   a. Caninized anti-canine IL-$4R_{\alpha}$ monoclonal antibodies
   b. c146E2-H3L3
   c. 4H3 caninized antibodies from US2018/0346580

Antibodies against canine IL-4 receptor alpha were tested for their ability to inhibit STAT-6 phosphorylation in DH82 Cell as follows:

Methods

1. Two tissue culture plates were seeded with $8\times10^4$ DH82 cells per well (200 μL with the density of $4\times10^5$ cells/mL) and incubated at 37° C. overnight.
2. The test antibodies were pre-diluted to 500 μg/mL and then 3-fold serially diluted in DH82 Cell Growth Media. The media was removed from the cell culture plates and 50 μL/well of the serially diluted test sample were transferred to each plate.
3. Canine IL-4 was diluted to 5 ng/mL in DH82 Cell Growth Media and 50 μL was added to each well of one plate. Canine IL-13 was diluted to 10 ng/mL in DH82 Cell Growth Media and 50 μL was added to each well of the second plate. The plates were incubated for 15 min at 37° C.
4. The media was removed from the plates and 100 μL per well of freshly prepared 1× lysis buffer from the AlphaLISA p-STAT-6 Assay Kit was added to the plate. The plate was agitated on a plate shaker with 350 rpm for 10 minutes at room temperature.
5. The Acceptor Mix was prepared from the AlphaLISA p-STAT6 Assay Kit and 15 per well was added to 30 μL of the cell lysate in 96-well 1/2 Area Plates. The plates were sealed, agitated for 2 minutes at 350 rpm, and then incubated for 2 hours at room temperature.
6. The Donor Mix was prepared from the AlphaLISA p-STAT6 Assay kit under subdued laboratory lighting and 15 μL per well was added to each plate. The plates were sealed, covered with foil, agitated for 2 minutes at 350 rpm, and then incubated for 2 hours at room temperature.
7. The plates were read using the AlphaScreen settings on the Perkin Elmer EnVison.

The two different caninized monoclonal anti-canine IL-$4R_{\alpha}$ antibodies designated c4H3 [WO2016/156588; US2018/0346580], and c146E2-H3L3 were evaluated for their ability to inhibit αSTAT-6 phosphorylation by blocking the binding of either canine IL-4 or canine IL-13 to canine IL-$4R_{\alpha}$. The data shown in FIG. 1 demonstrate that both antibodies result in a dose-dependent inhibition of STAT-6 phosphorylation in the presence of IL-4, but surprisingly, c146E2-H3L3 bound more tightly than the prior art anti-canine IL-4 receptor alpha antibody c4H3 [WO2016/156588]. The IL-4 control in the absence of IL-4R alpha (IL-$4R_{\alpha}$) antibodies is shown in the upper right-hand portion of the graph. The data shown in FIG. 2 also demonstrates that that both antibodies result in a dose dependent inhibition of STAT-6 phosphorylation in the presence of IL-13, with c146E2-H3L3 again binding more tightly than the prior art anti-canine IL-4 receptor alpha antibody c4H3. The IL-13 control in the absence of IL-4R alpha (IL-$4R_{\alpha}$) antibodies is shown in the upper right hand portion of the graph. FIG. 3 shows that replacing the kappa light chain with the lambda light chain had no effect on the binding of c146E2-H3L3 to IL-4R alpha.

Example 3

Epitope Mapping

The interaction of antibodies with their cognate protein antigens is mediated through the binding of specific amino acids of the antibodies (paratopes) with specific amino acids (epitopes) of target antigens. An epitope is an antigenic determinant that causes a specific reaction by an immunoglobulin. An epitope consists of a group of amino acids on the surface of the antigen. A protein of interest may contain several epitopes that are recognized by different antibodies. The epitopes recognized by antibodies are classified as linear or conformational epitopes. Linear epitopes are formed by a stretch of a continuous sequence of amino acids in a protein, while conformational epitopes are composed of amino acids that are discontinuous (e.g., far apart) in the primary amino acid sequence, but are brought together upon three-dimensional protein folding.

Epitope mapping refers to the process of identifying the amino acid sequences (i.e., epitopes) that are recognized by antibodies on their target antigens. Identification of epitopes recognized by monoclonal antibodies (mAbs) on target antigens has important applications. For example, it can aid in the development of new therapeutics, diagnostics, and vaccines. Epitope mapping can also aid in the selection of optimized therapeutic mAbs and help elucidate their mechanisms of action. Epitope information on IL-4 receptor alpha can also elucidate unique epitopes, and define the protective or pathogenic effects of vaccines. Epitope identification also can lead to development of subunit vaccines based on chemical or genetic coupling of the identified peptide epitope to a carrier protein or other immunostimulating agents.

Epitope mapping can be carried out using polyclonal or monoclonal antibodies and several methods are employed for epitope identification depending on the suspected nature of the epitope (i.e., linear versus conformational). Mapping linear epitopes is more straightforward and relatively, easier to perform. For this purpose, commercial services for linear epitope mapping often employ peptide scanning. In this case, an overlapping set of short peptide sequences of the target protein are chemically synthesized and tested for their ability to bind antibodies of interest. The strategy is rapid, high-throughput, and relatively inexpensive to perform. On the other hand, mapping of a discontinuous epitope is more technically challenging and requires more specialized techniques such as x-ray co-crystallography of a monoclonal antibody together with its target protein, Hydrogen-Deuterium (H/D) exchange, Mass Spectrometry coupled with enzymatic digestion as well as several other methods known to those skilled in the art.

Mapping of Canine IL-4 Receptor Alpha Epitopes Using Mass Spectroscopy:

A method based on chemical crosslinking, mass spectrometry detection, and covalent tagging as employed to identify epitopes recognized by anti-canine IL-4 receptor alpha mAbs [CovalX Instruments Incorporated located at 999 Broadway, Suite 305, Saugus, Mass. 01906-4510 USA).]

Figure 4:
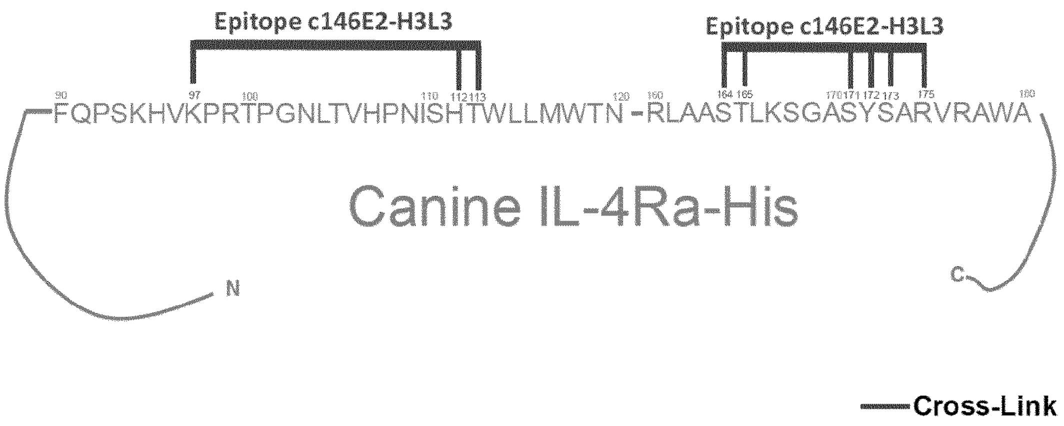
FIG. 4 shows the epitope comprising amino acid sequences SEQ ID NO: 46 and SEQ ID NO: 47 on canine IL-4$R_{\alpha}$ for the c146E2-H3L3 antibody.

The application of this technology to epitope mapping of canine IL-4 receptor alpha chain in a prior study indicated that the mAbs recognize specific peptide epitopes that are present within the extracellular domain of canine IL-4 receptor alpha [US2018/0346580]. Similar analysis performed for the c146E2-H3L3 antibody to canine IL-4 receptor alpha displayed in FIG. 4, resulted in the identification of amino acid sequences SEQ ID NO: 46 and SEQ ID NO: 47 for epitope(s) that have a reasonable similarity to those previously identified. In addition, as displayed in FIG. 4, amino acid residues $K_{97}$, $H_{112}$, $T_{113}$, $S_{164}$, $T_{165}$, $S_{171}$, $Y_{172}$, $S_{173}$, and $R_{175}$, were identified as particular contact points [see e.g., SEQ ID NO: 5, for amino acid residue numbering].

SEQUENCE LISTING TABLE

| SEQ ID NO: | | NA | AA |
|---|---|---|---|
| 1 | Canine IL-4 receptor α chain with signal sequence | ✓ | |
| 2 | Canine IL-4 receptor α chain with signal sequence | | ✓ |
| 3 | Canine IL-4 receptor α chain without signal sequence | ✓ | |
| 4 | Canine IL-4 receptor α chain without signal sequence | | ✓ |
| 5 | Canine IL-4 receptor α extracellular domain | | ✓ |
| 6 | IgG-A hinge region | | ✓ |
| 7 | IgG-B hinge region | | ✓ |
| 8 | IgG-C hinge region | | ✓ |
| 9 | Modified IgG-D hinge region | | ✓ |
| 10 | Canine IgG-Bm | | ✓ |
| 11 | 146 E2 HCDR1 | ✓ | |
| 12 | 146 E2 HCDR1 | | ✓ |
| 13 | 146 E2 HCDR2 | ✓ | |
| 14 | 146 E2 HCDR2 | | ✓ |
| 15 | 146 E2 HCDR3 | ✓ | |
| 16 | 146 E2 HCDR3 | | ✓ |

-continued

SEQUENCE LISTING TABLE

| SEQ ID NO: | | NA | AA |
|---|---|---|---|
| 17 | 146 E2 LCDR1 | ✓ | |
| 18 | 146 E2 LCDR1 | | ✓ |
| 19 | 146 E2 LCDR2 | ✓ | |
| 20 | 146 E2 LCDR2 | | ✓ |
| 21 | 146 E2 LCDR3 | ✓ | |
| 22 | 146 E2 LCDR3 | | ✓ |
| 23 | 152 H11 HCDR1 | ✓ | |
| 24 | 152 H11 HCDR1 | | ✓ |
| 25 | 152 H11 HCDR2 | ✓ | |
| 26 | 152 H11 HCDR2 | | ✓ |
| 27 | 152 H11 HCDR3 | ✓ | |
| 28 | 152 H11 HCDR3 | | ✓ |
| 29 | 152 H11 LCDR1 | ✓ | |
| 30 | 152 H11 LCDR1 | | ✓ |
| 31 | 152 H11 LCDR2 | ✓ | |
| 32 | 152 H11 LCDR2 | | ✓ |
| 33 | 152 H11 LCDR3 | ✓ | |
| 34 | 152 H11 LCDR3 | | ✓ |
| 35 | C152H11VL3-cCLk-s (kappa light chain) | | ✓ |
| 36 | C152H11VH1-cIgG-Bm (heavy chain) | | ✓ |
| 37 | C152H11VH2-cIgG-Bm (heavy chain) | | ✓ |
| 38 | C152H11VH3-cIgG-Bm (heavy chain) | | ✓ |
| 39 | c146E2VL3-cCLk-s (kappa light chain) | | ✓ |
| 40 | c146E2VH1-cIgG-Bm (heavy chain) | | ✓ |
| 41 | c146E2VH2-cIgG-Bm (heavy chain) | | ✓ |
| 42 | c146E2VH3-cIgG-Bm (heavy chain) | | ✓ |
| 43 | c152H11LV1-cCl (lambda light chain) | | ✓ |
| 44 | c146E2LV1-cCl (lambda light chain) | | ✓ |
| 45 | Canine IgG-B | | ✓ |
| 46 | FQPSKHVKPRTPGNLTVHPNISHTWLLMWTN | | ✓ |
| 47 | RLAASTLKSGASYSARVRAWA | | ✓ |

We claim:

1. An isolated mammalian antibody or antigen binding fragment thereof that binds canine interleukin-4 receptor α ($IL\text{-}4R_{\alpha}$) comprising a set of six complementary determining regions (CDRs), three of which are heavy chain CDRs: a CDR heavy 1 (HCDR1), a CDR heavy 2 (HCDR2), and a CDR heavy 3 (HCDR3) and three of which are light chain CDRs: a CDR light 1 (LCDR1), a CDR light 2 (LCDR2), and a CDR light 3 (LCDR3); wherein (i) the HCDR1 comprises the amino acid sequence of SEQ ID NO: 12;

(ii) the HCDR2 comprises the amino acid sequence of SEQ ID NO: 14;

(iii) the HCDR3 comprises the amino acid sequence of SEQ ID NO: 16;

(iv) the LCDR1 comprises the amino acid sequence of SEQ ID NO: 18;

(v) the LCDR2 comprises the amino acid sequence of SEQ ID NO: 20; and (vi) the LCDR3 comprises the amino acid sequence of SEQ ID NO: 22.

2. The isolated mammalian antibody or antigen binding fragment thereof of claim 1, wherein the antibody and antigen binding fragment thereof bind canine IL-4Ra and block the binding of canine IL-4Ra to canine interleukin-4.

3. The isolated mammalian antibody or antigen binding fragment thereof of claim 1, that is a caninized antibody or a caninized antigen binding fragment thereof.

4. The caninized antibody or caninized antigen binding fragment thereof of claim 3, comprising a hinge region comprising the amino acid sequence selected from the group consisting of SEQ ID NO: 6, SEQ ID NO: 7, SEQ ID NO: 8, and SEQ ID NO: 9.

5. The caninized antibody or caninized antigen binding fragment thereof of claim 3, comprising a heavy chain comprising a modified canine IgG-B (IgG-Bm) comprising the amino acid sequence of SEQ ID NO: 10.

6. The caninized antibody or caninized antigen binding fragment thereof of claim 5, comprising a heavy chain comprising an amino acid sequence selected from the group consisting of SEQ ID NO: 40, SEQ ID NO: 41, and SEQ ID NO: 42.

7. An isolated caninized mammalian antibody or caninized antigen binding fragment thereof that binds canine interleukin-4 receptor α ($IL\text{-}4R_{\alpha}$), comprising a light chain comprising the amino acid sequence SEQ ID NO: 39 and a heavy chain comprising an amino acid sequence selected from the group consisting of SEQ ID NO: 40, SEQ ID NO: 41, and SEQ ID NO: 42.

8. An isolated caninized mammalian antibody or caninized antigen binding fragment thereof that binds canine interleukin-4 receptor α ($IL\text{-}4R_{\alpha}$), comprising a light chain comprising the amino acid sequence SEQ ID NO: 44 and a heavy chain comprising an amino acid sequence selected from the group consisting of SEQ ID NO: 40, SEQ ID NO: 41, and SEQ ID NO: 42.

9. An isolated nucleic acid that encodes the heavy chain of the caninized antibody or caninized antigen binding fragment thereof of claim 3.

10. An isolated nucleic acid that encodes the light chain of the caninized antibody or caninized antigen binding fragment thereof of claim 3.

11. An expression vector comprising the isolated nucleic acid of claim 9.

12. A host cell comprising the expression vector of claim 11.

13. A pharmaceutical composition comprising the caninized antibody or caninized antigen binding fragment thereof of claim 3, and a pharmaceutically acceptable carrier or diluent.

14. A method of aiding in the blocking of inflammation associated with atopic dermatitis, comprising administering to a subject in need thereof a therapeutically effective amount of the pharmaceutical composition of claim 13.

15. An expression vector comprising the isolated nucleic acid of claim 10.

16. A host cell comprising the expression vector of claim 15.

17. A pharmaceutical composition comprising the caninized antibody or caninized antigen binding fragment thereof of claim 8, and a pharmaceutically acceptable carrier or diluent.

18. A method of aiding in the blocking of inflammation associated with atopic dermatitis, comprising administering to a subject in need thereof a therapeutically effective amount of the pharmaceutical composition of claim 17.

19. A pharmaceutical composition comprising the caninized antibody or caninized antigen binding fragment thereof of claim 7, and a pharmaceutically acceptable carrier or diluent.

20. A method of aiding in the blocking of inflammation associated with atopic dermatitis, comprising administering to a subject in need thereof a therapeutically effective amount of the pharmaceutical composition of claim 19.

* * * * *

SEQUENCE LISTING

<160> NUMBER OF SEQ ID NOS: 47

<210> SEQ ID NO 1
<211> LENGTH: 2469
<212> TYPE: DNA
<213> ORGANISM: Canis familiaris -continued

<400> SEQUENCE: 1

```
atgggcagac tgtgcagcgg cctgaccttc cccgtgagct gcctggtgct ggtgtgggtg     60
gccagcagcg gcagcgtgaa ggtgctgcac gagcccagct gcttcagcga ctacatcagc    120
accagcgtgt gccagtggaa gatggaccac cccaccaact gcagcgccga gctgagactg    180
agctaccagc tggacttcat gggcagcgag aaccacacct gcgtgcccga gaacagagag    240
gacagcgtgt gcgtgtgcag catgcccatc gacgacgccg tggaggccga cgtgtaccag    300
ctggacctgt gggccggcca gcagctgctg tggagcggca gcttccagcc cagcaagcac    360
gtgaagccca gaacccccgg caacctgacc gtgcaccccca acatcagcca cacctggctg    420
ctgatgtgga ccaaccccta ccccaccgag aaccacctgc acagcgagct gacctacatg    480
gtgaacgtga gcaacgacaa cgaccccgag gacttcaagg tgtacaacgt gacctacatg    540
ggccccaccc tgagactggc cgccagcacc ctgaagagcg gcgccagcta cagcgccaga    600
gtgagagcct gggcccagac ctacaacagc acctggagcg actggagccc cagcaccacc    660
tggctgaact actacgagcc ctgggagcag cacctgcccc tgggcgtgag catcagctgc    720
ctggtgatcc tggccatctg cctgagctgc tacttcagca tcatcaagat caagaagggc    780
tggtgggacc agatccccaa ccccgcccac agccccctgg tggccatcgt gatccaggac    840
agccaggtga gcctgtgggg caagagaagc agaggccagg agcccgccaa gtgcccccac    900
tggaagacct gcctgaccaa gctgctgccc tgcctgctgg agcacggcct gggcagagag    960
gaggagagcc ccaagaccgc caagaacggc cccctgcagg gccccggcaa gcccgcctgg   1020
tgccccgtgg aggtgagcaa gaccatcctg tggcccgaga gcatcagcgt ggtgcagtgc   1080
gtggagctga gcgaggcccc cgtggacaac gaggaggagg aggaggtgga ggaggacaag   1140
agaagcctgt gccccagcct ggagggcagc ggcggcagct tccaggaggg cagagagggc   1200
atcgtggcca gactgaccga gagcctgttc ctggacctgc tgggcggcga gaacggcggc   1260
ttctgccccc agggcctgga ggagagctgc ctgccccccc ccagcggcag cgtgggcgcc   1320
cagatgccct gggcccagtt ccccagagcc ggccccagag ccgcccccga gggccccgag   1380
cagcccagaa gacccgagag cgccctgcag gccagcccca cccagagcgc cggcagcagc   1440
gccttccccg agccccccc cgtggtgacc gacaaccccg cctacagaag cttcggcagc   1500
ttcctgggcc agagcagcga ccccggcgac ggcgacagcg accccgagct ggccgacaga   1560
cccggcgagg ccgaccccgg catccccagc gccccccagc cccccgagcc ccccgccgcc   1620
ctgcagcccg agcccgagag ctgggagcag atcctgagac agagcgtgct gcagcacaga   1680
gccgcccccg cccccggccc cggccccggc agcggctaca gagagttcac ctgcgccgtg   1740
aagcagggca gcgcccccga cgccggcggc cccggcttcg gccccagcgg cgaggccggc   1800
tacaaggcct tctgcagcct gctgcccggc ggcgccacct gccccggcac cagcggcggc   1860
gaggccggca gcggcgaggg cggctacaag cccttccaga gcctgacccc cggctgcccc   1920
ggcgccccca cccccgtgcc cgtgcccctg ttcaccttcg gcctggacac cgagcccccc   1980
ggcagccccc aggacagcct gggcgccggc agcagccccg agcacctggg cgtggagccc   2040
gccggcaagg aggaggacag cagaaagacc ctgctggccc ccgagcaggc caccgacccc   2100
ctgagagacg acctggccag cagcatcgtg tacagcgccc tgacctgcca cctgtgcggc   2160
cacctgaagc agtggcacga ccaggaggag agaggcaagg cccacatcgt gcccagcccc   2220
tgctgcggct gctgctgcgg cgacagaagc agcctgctgc tgagccccct gagagccccc   2280
```

```
aacgtgctgc ccggcggcgt gctgctggag gccagcctga gccccgccag cctggtgccc   2340

agcggcgtga gcaaggaggg caagagcagc cccttcagcc agcccgccag cagcagcgcc   2400

cagagcagca gccagacccc caagaagctg gccgtgctga gcaccgagcc cacctgcatg   2460

agcgccagc                                                           2469


<210> SEQ ID NO 2
<211> LENGTH: 823
<212> TYPE: PRT
<213> ORGANISM: Canis familiaris

<400> SEQUENCE: 2

Met Gly Arg Leu Cys Ser Gly Leu Thr Phe Pro Val Ser Cys Leu Val
1               5                   10                  15

Leu Val Trp Val Ala Ser Ser Gly Ser Val Lys Val Leu His Glu Pro
            20                  25                  30

Ser Cys Phe Ser Asp Tyr Ile Ser Thr Ser Val Cys Gln Trp Lys Met
        35                  40                  45

Asp His Pro Thr Asn Cys Ser Ala Glu Leu Arg Leu Ser Tyr Gln Leu
    50                  55                  60

Asp Phe Met Gly Ser Glu Asn His Thr Cys Val Pro Glu Asn Arg Glu
65                  70                  75                  80

Asp Ser Val Cys Val Cys Ser Met Pro Ile Asp Asp Ala Val Glu Ala
                85                  90                  95

Asp Val Tyr Gln Leu Asp Leu Trp Ala Gly Gln Gln Leu Leu Trp Ser
            100                 105                 110

Gly Ser Phe Gln Pro Ser Lys His Val Lys Pro Arg Thr Pro Gly Asn
        115                 120                 125

Leu Thr Val His Pro Asn Ile Ser His Thr Trp Leu Leu Met Trp Thr
    130                 135                 140

Asn Pro Tyr Pro Thr Glu Asn His Leu His Ser Glu Leu Thr Tyr Met
145                 150                 155                 160

Val Asn Val Ser Asn Asp Asn Asp Pro Glu Asp Phe Lys Val Tyr Asn
                165                 170                 175

Val Thr Tyr Met Gly Pro Thr Leu Arg Leu Ala Ala Ser Thr Leu Lys
            180                 185                 190

Ser Gly Ala Ser Tyr Ser Ala Arg Val Arg Ala Trp Ala Gln Thr Tyr
        195                 200                 205

Asn Ser Thr Trp Ser Asp Trp Ser Pro Ser Thr Thr Trp Leu Asn Tyr
    210                 215                 220

Tyr Glu Pro Trp Glu Gln His Leu Pro Leu Gly Val Ser Ile Ser Cys
225                 230                 235                 240

Leu Val Ile Leu Ala Ile Cys Leu Ser Cys Tyr Phe Ser Ile Ile Lys
                245                 250                 255

Ile Lys Lys Gly Trp Trp Asp Gln Ile Pro Asn Pro Ala His Ser Pro
            260                 265                 270

Leu Val Ala Ile Val Ile Gln Asp Ser Gln Val Ser Leu Trp Gly Lys
        275                 280                 285

Arg Ser Arg Gly Gln Glu Pro Ala Lys Cys Pro His Trp Lys Thr Cys
    290                 295                 300

Leu Thr Lys Leu Leu Pro Cys Leu Leu Glu His Gly Leu Gly Arg Glu
305                 310                 315                 320

Glu Glu Ser Pro Lys Thr Ala Lys Asn Gly Pro Leu Gln Gly Pro Gly
                325                 330                 335
```

-continued

```
Lys Pro Ala Trp Cys Pro Val Glu Val Ser Lys Thr Ile Leu Trp Pro
            340                 345                 350

Glu Ser Ile Ser Val Val Gln Cys Val Glu Leu Ser Glu Ala Pro Val
        355                 360                 365

Asp Asn Glu Glu Glu Glu Glu Val Glu Glu Asp Lys Arg Ser Leu Cys
    370                 375                 380

Pro Ser Leu Glu Gly Ser Gly Gly Ser Phe Gln Glu Gly Arg Glu Gly
385                 390                 395                 400

Ile Val Ala Arg Leu Thr Glu Ser Leu Phe Leu Asp Leu Leu Gly Gly
                405                 410                 415

Glu Asn Gly Gly Phe Cys Pro Gln Gly Leu Glu Glu Ser Cys Leu Pro
            420                 425                 430

Pro Pro Ser Gly Ser Val Gly Ala Gln Met Pro Trp Ala Gln Phe Pro
        435                 440                 445

Arg Ala Gly Pro Arg Ala Ala Pro Glu Gly Pro Glu Gln Pro Arg Arg
    450                 455                 460

Pro Glu Ser Ala Leu Gln Ala Ser Pro Thr Gln Ser Ala Gly Ser Ser
465                 470                 475                 480

Ala Phe Pro Glu Pro Pro Pro Val Val Thr Asp Asn Pro Ala Tyr Arg
                485                 490                 495

Ser Phe Gly Ser Phe Leu Gly Gln Ser Ser Asp Pro Gly Asp Gly Asp
            500                 505                 510

Ser Asp Pro Glu Leu Ala Asp Arg Pro Gly Glu Ala Asp Pro Gly Ile
        515                 520                 525

Pro Ser Ala Pro Gln Pro Pro Glu Pro Pro Ala Ala Leu Gln Pro Glu
    530                 535                 540

Pro Glu Ser Trp Glu Gln Ile Leu Arg Gln Ser Val Leu Gln His Arg
545                 550                 555                 560

Ala Ala Pro Ala Pro Gly Pro Gly Pro Gly Ser Gly Tyr Arg Glu Phe
                565                 570                 575

Thr Cys Ala Val Lys Gln Gly Ser Ala Pro Asp Ala Gly Gly Pro Gly
            580                 585                 590

Phe Gly Pro Ser Gly Glu Ala Gly Tyr Lys Ala Phe Cys Ser Leu Leu
        595                 600                 605

Pro Gly Gly Ala Thr Cys Pro Gly Thr Ser Gly Gly Glu Ala Gly Ser
    610                 615                 620

Gly Glu Gly Gly Tyr Lys Pro Phe Gln Ser Leu Thr Pro Gly Cys Pro
625                 630                 635                 640

Gly Ala Pro Thr Pro Val Pro Val Pro Leu Phe Thr Phe Gly Leu Asp
                645                 650                 655

Thr Glu Pro Pro Gly Ser Pro Gln Asp Ser Leu Gly Ala Gly Ser Ser
            660                 665                 670

Pro Glu His Leu Gly Val Glu Pro Ala Gly Lys Glu Glu Asp Ser Arg
        675                 680                 685

Lys Thr Leu Leu Ala Pro Glu Gln Ala Thr Asp Pro Leu Arg Asp Asp
    690                 695                 700

Leu Ala Ser Ser Ile Val Tyr Ser Ala Leu Thr Cys His Leu Cys Gly
705                 710                 715                 720

His Leu Lys Gln Trp His Asp Gln Glu Glu Arg Gly Lys Ala His Ile
                725                 730                 735

Val Pro Ser Pro Cys Cys Gly Cys Cys Cys Gly Asp Arg Ser Ser Leu
            740                 745                 750

Leu Leu Ser Pro Leu Arg Ala Pro Asn Val Leu Pro Gly Gly Val Leu
```

-continued

```
        755                 760                 765

Leu Glu Ala Ser Leu Ser Pro Ala Ser Leu Val Pro Ser Gly Val Ser
    770                 775                 780

Lys Glu Gly Lys Ser Ser Pro Phe Ser Gln Pro Ala Ser Ser Ser Ala
785                 790                 795                 800

Gln Ser Ser Ser Gln Thr Pro Lys Lys Leu Ala Val Leu Ser Thr Glu
                805                 810                 815

Pro Thr Cys Met Ser Ala Ser
            820


<210> SEQ ID NO 3
<211> LENGTH: 2394
<212> TYPE: DNA
<213> ORGANISM: Canis familiaris

<400> SEQUENCE: 3

gtgaaggtgc tgcacgagcc cagctgcttc agcgactaca tcagcaccag cgtgtgccag     60

tggaagatgg accaccccac caactgcagc gccgagctga gactgagcta ccagctggac    120

ttcatgggca gcgagaacca cacctgcgtg cccgagaaca gagaggacag cgtgtgcgtg    180

tgcagcatgc ccatcgacga cgccgtggag gccgacgtgt accagctgga cctgtgggcc    240

ggccagcagc tgctgtggag cggcagcttc cagcccagca agcacgtgaa gcccagaacc    300

cccggcaacc tgaccgtgca ccccaacatc agccacacct ggctgctgat gtggaccaac    360

ccctacccca ccgagaacca cctgcacagc gagctgacct acatggtgaa cgtgagcaac    420

gacaacgacc ccgaggactt caaggtgtac aacgtgacct acatgggccc caccctgaga    480

ctggccgcca gcaccctgaa gagcggcgcc agctacagcg ccagagtgag agcctgggcc    540

cagacctaca acagcacctg gagcgactgg agccccagca ccacctggct gaactactac    600

gagccctggg agcagcacct gcccctgggc gtgagcatca gctgcctggt gatcctggcc    660

atctgcctga gctgctactt cagcatcatc aagatcaaga agggctggtg ggaccagatc    720

cccaaccccg cccacagccc cctggtggcc atcgtgatcc aggacagcca ggtgagcctg    780

tggggcaaga gaagcagagg ccaggagccc gccaagtgcc cccactggaa gacctgcctg    840

accaagctgc tgccctgcct gctggagcac ggcctgggca gagaggagga gagccccaag    900

accgccaaga acggccccct gcagggcccc ggcaagcccg cctggtgccc cgtggaggtg    960

agcaagacca tcctgtggcc cgagagcatc agcgtggtgc agtgcgtgga gctgagcgag   1020

gcccccgtgg acaacgagga ggaggaggag gtggaggagg acaagagaag cctgtgcccc   1080

agcctggagg gcagcggcgg cagcttccag gagggcagag agggcatcgt ggccagactg   1140

accgagagcc tgttcctgga cctgctgggc ggcgagaacg gcggcttctg cccccagggc   1200

ctggaggaga gctgcctgcc cccccccagc ggcagcgtgg gcgcccagat gccctgggcc   1260

cagttcccca gagccggccc cagagccgcc cccgagggcc ccgagcagcc cagaagaccc   1320

gagagcgccc tgcaggccag ccccacccag agcgccggca gcagcgcctt ccccgagccc   1380

ccccccgtgg tgaccgacaa ccccgcctac agaagcttcg gcagcttcct gggccagagc   1440

agcgaccccg gcgacggcga cagcgacccc gagctggccg acagacccgg cgaggccgac   1500

cccggcatcc ccagcgcccc ccagcccccc gagcccccccg ccgccctgca gcccgagccc  1560

gagagctggg agcagatcct gagacagagc gtgctgcagc acagagccgc ccccgccccc   1620

ggccccggcc ccggcagcgg ctacagagag ttcacctgcg ccgtgaagca gggcagcgcc   1680

cccgacgccg gcggccccgg cttcggcccc agcggcgagg ccggctacaa ggccttctgc   1740
```

-continued

```
agcctgctgc ccggcggcgc cacctgcccc ggcaccagcg gcggcgaggc cggcagcggc   1800

gagggcggct acaagccctt ccagagcctg acccccggct gccccggcgc ccccaccccc   1860

gtgcccgtgc ccctgttcac cttcggcctg gacaccgagc cccccggcag cccccaggac   1920

agcctgggcg ccggcagcag ccccgagcac ctgggcgtgg agcccgccgg caaggaggag   1980

gacagcagaa agaccctgct ggcccccgag caggccaccg accccctgag agacgacctg   2040

gccagcagca tcgtgtacag cgccctgacc tgccacctgt gcggccacct gaagcagtgg   2100

cacgaccagg aggagagagg caaggcccac atcgtgccca gcccctgctg cggctgctgc   2160

tgcggcgaca gaagcagcct gctgctgagc cccctgagag cccccaacgt gctgcccggc   2220

ggcgtgctgc tggaggccag cctgagcccc gccagcctgg tgcccagcgg cgtgagcaag   2280

gagggcaaga gcagcccctt cagccagccc gccagcagca gcgcccagag cagcagccag   2340

acccccaaga agctggccgt gctgagcacc gagcccacct gcatgagcgc cagc         2394
```

<210> SEQ ID NO 4
<211> LENGTH: 798
<212> TYPE: PRT
<213> ORGANISM: Canis familiaris

<400> SEQUENCE: 4

```
Val Lys Val Leu His Glu Pro Ser Cys Phe Ser Asp Tyr Ile Ser Thr
1               5                   10                  15

Ser Val Cys Gln Trp Lys Met Asp His Pro Thr Asn Cys Ser Ala Glu
            20                  25                  30

Leu Arg Leu Ser Tyr Gln Leu Asp Phe Met Gly Ser Glu Asn His Thr
        35                  40                  45

Cys Val Pro Glu Asn Arg Glu Asp Ser Val Cys Val Cys Ser Met Pro
    50                  55                  60

Ile Asp Asp Ala Val Glu Ala Asp Val Tyr Gln Leu Asp Leu Trp Ala
65                  70                  75                  80

Gly Gln Gln Leu Leu Trp Ser Gly Ser Phe Gln Pro Ser Lys His Val
                85                  90                  95

Lys Pro Arg Thr Pro Gly Asn Leu Thr Val His Pro Asn Ile Ser His
            100                 105                 110

Thr Trp Leu Leu Met Trp Thr Asn Pro Tyr Pro Thr Glu Asn His Leu
        115                 120                 125

His Ser Glu Leu Thr Tyr Met Val Asn Val Ser Asn Asp Asn Asp Pro
    130                 135                 140

Glu Asp Phe Lys Val Tyr Asn Val Thr Tyr Met Gly Pro Thr Leu Arg
145                 150                 155                 160

Leu Ala Ala Ser Thr Leu Lys Ser Gly Ala Ser Tyr Ser Ala Arg Val
                165                 170                 175

Arg Ala Trp Ala Gln Thr Tyr Asn Ser Thr Trp Ser Asp Trp Ser Pro
            180                 185                 190

Ser Thr Thr Trp Leu Asn Tyr Tyr Glu Pro Trp Glu Gln His Leu Pro
        195                 200                 205

Leu Gly Val Ser Ile Ser Cys Leu Val Ile Leu Ala Ile Cys Leu Ser
    210                 215                 220

Cys Tyr Phe Ser Ile Ile Lys Ile Lys Lys Gly Trp Trp Asp Gln Ile
225                 230                 235                 240

Pro Asn Pro Ala His Ser Pro Leu Val Ala Ile Val Ile Gln Asp Ser
                245                 250                 255
```

-continued

```
Gln Val Ser Leu Trp Gly Lys Arg Ser Arg Gly Gln Glu Pro Ala Lys
            260                 265                 270

Cys Pro His Trp Lys Thr Cys Leu Thr Lys Leu Leu Pro Cys Leu Leu
        275                 280                 285

Glu His Gly Leu Gly Arg Glu Glu Glu Ser Pro Lys Thr Ala Lys Asn
    290                 295                 300

Gly Pro Leu Gln Gly Pro Gly Lys Pro Ala Trp Cys Pro Val Glu Val
305                 310                 315                 320

Ser Lys Thr Ile Leu Trp Pro Glu Ser Ile Ser Val Val Gln Cys Val
                325                 330                 335

Glu Leu Ser Glu Ala Pro Val Asp Asn Glu Glu Glu Glu Glu Val Glu
            340                 345                 350

Glu Asp Lys Arg Ser Leu Cys Pro Ser Leu Glu Gly Ser Gly Gly Ser
        355                 360                 365

Phe Gln Glu Gly Arg Glu Gly Ile Val Ala Arg Leu Thr Glu Ser Leu
    370                 375                 380

Phe Leu Asp Leu Leu Gly Gly Glu Asn Gly Gly Phe Cys Pro Gln Gly
385                 390                 395                 400

Leu Glu Glu Ser Cys Leu Pro Pro Pro Ser Gly Ser Val Gly Ala Gln
                405                 410                 415

Met Pro Trp Ala Gln Phe Pro Arg Ala Gly Pro Arg Ala Ala Pro Glu
            420                 425                 430

Gly Pro Glu Gln Pro Arg Arg Pro Glu Ser Ala Leu Gln Ala Ser Pro
        435                 440                 445

Thr Gln Ser Ala Gly Ser Ser Ala Phe Pro Glu Pro Pro Pro Val Val
    450                 455                 460

Thr Asp Asn Pro Ala Tyr Arg Ser Phe Gly Ser Phe Leu Gly Gln Ser
465                 470                 475                 480

Ser Asp Pro Gly Asp Gly Asp Ser Asp Pro Glu Leu Ala Asp Arg Pro
                485                 490                 495

Gly Glu Ala Asp Pro Gly Ile Pro Ser Ala Pro Gln Pro Pro Glu Pro
            500                 505                 510

Pro Ala Ala Leu Gln Pro Glu Pro Glu Ser Trp Glu Gln Ile Leu Arg
        515                 520                 525

Gln Ser Val Leu Gln His Arg Ala Ala Pro Ala Pro Gly Pro Gly Pro
    530                 535                 540

Gly Ser Gly Tyr Arg Glu Phe Thr Cys Ala Val Lys Gln Gly Ser Ala
545                 550                 555                 560

Pro Asp Ala Gly Gly Pro Gly Phe Gly Pro Ser Gly Glu Ala Gly Tyr
                565                 570                 575

Lys Ala Phe Cys Ser Leu Leu Pro Gly Gly Ala Thr Cys Pro Gly Thr
            580                 585                 590

Ser Gly Gly Glu Ala Gly Ser Gly Glu Gly Gly Tyr Lys Pro Phe Gln
        595                 600                 605

Ser Leu Thr Pro Gly Cys Pro Gly Ala Pro Thr Pro Val Pro Val Pro
    610                 615                 620

Leu Phe Thr Phe Gly Leu Asp Thr Glu Pro Pro Gly Ser Pro Gln Asp
625                 630                 635                 640

Ser Leu Gly Ala Gly Ser Ser Pro Glu His Leu Gly Val Glu Pro Ala
                645                 650                 655

Gly Lys Glu Glu Asp Ser Arg Lys Thr Leu Leu Ala Pro Glu Gln Ala
            660                 665                 670

Thr Asp Pro Leu Arg Asp Asp Leu Ala Ser Ser Ile Val Tyr Ser Ala
```

-continued

```
        675                 680                 685

Leu Thr Cys His Leu Cys Gly His Leu Lys Gln Trp His Asp Gln Glu
    690                 695                 700

Glu Arg Gly Lys Ala His Ile Val Pro Ser Pro Cys Cys Gly Cys Cys
705                 710                 715                 720

Cys Gly Asp Arg Ser Ser Leu Leu Leu Ser Pro Leu Arg Ala Pro Asn
                725                 730                 735

Val Leu Pro Gly Gly Val Leu Leu Glu Ala Ser Leu Ser Pro Ala Ser
            740                 745                 750

Leu Val Pro Ser Gly Val Ser Lys Glu Gly Lys Ser Ser Pro Phe Ser
        755                 760                 765

Gln Pro Ala Ser Ser Ser Ala Gln Ser Ser Ser Gln Thr Pro Lys Lys
    770                 775                 780

Leu Ala Val Leu Ser Thr Glu Pro Thr Cys Met Ser Ala Ser
785                 790                 795


<210> SEQ ID NO 5
<211> LENGTH: 208
<212> TYPE: PRT
<213> ORGANISM: Canis familiaris

<400> SEQUENCE: 5

Val Lys Val Leu His Glu Pro Ser Cys Phe Ser Asp Tyr Ile Ser Thr
1               5                   10                  15

Ser Val Cys Gln Trp Lys Met Asp His Pro Thr Asn Cys Ser Ala Glu
            20                  25                  30

Leu Arg Leu Ser Tyr Gln Leu Asp Phe Met Gly Ser Glu Asn His Thr
        35                  40                  45

Cys Val Pro Glu Asn Arg Glu Asp Ser Val Cys Val Cys Ser Met Pro
    50                  55                  60

Ile Asp Asp Ala Val Glu Ala Asp Val Tyr Gln Leu Asp Leu Trp Ala
65                  70                  75                  80

Gly Gln Gln Leu Leu Trp Ser Gly Ser Phe Gln Pro Ser Lys His Val
                85                  90                  95

Lys Pro Arg Thr Pro Gly Asn Leu Thr Val His Pro Asn Ile Ser His
            100                 105                 110

Thr Trp Leu Leu Met Trp Thr Asn Pro Tyr Pro Thr Glu Asn His Leu
        115                 120                 125

His Ser Glu Leu Thr Tyr Met Val Asn Val Ser Asn Asp Asn Asp Pro
    130                 135                 140

Glu Asp Phe Lys Val Tyr Asn Val Thr Tyr Met Gly Pro Thr Leu Arg
145                 150                 155                 160

Leu Ala Ala Ser Thr Leu Lys Ser Gly Ala Ser Tyr Ser Ala Arg Val
                165                 170                 175

Arg Ala Trp Ala Gln Thr Tyr Asn Ser Thr Trp Ser Asp Trp Ser Pro
            180                 185                 190

Ser Thr Thr Trp Leu Asn Tyr Tyr Glu Pro Trp Glu Gln His Leu Pro
        195                 200                 205


<210> SEQ ID NO 6
<211> LENGTH: 17
<212> TYPE: PRT
<213> ORGANISM: Canis familiaris

<400> SEQUENCE: 6

Phe Asn Glu Cys Arg Cys Thr Asp Thr Pro Pro Cys Pro Val Pro Glu
```

-continued

```
1               5                   10                  15

Pro


<210> SEQ ID NO 7
<211> LENGTH: 22
<212> TYPE: PRT
<213> ORGANISM: Canis familiaris

<400> SEQUENCE: 7

Pro Lys Arg Glu Asn Gly Arg Val Pro Arg Pro Pro Asp Cys Pro Lys
1               5                   10                  15

Cys Pro Ala Pro Glu Met
            20


<210> SEQ ID NO 8
<211> LENGTH: 20
<212> TYPE: PRT
<213> ORGANISM: Canis familiaris

<400> SEQUENCE: 8

Ala Lys Glu Cys Glu Cys Lys Cys Asn Cys Asn Asn Cys Pro Cys Pro
1               5                   10                  15

Gly Cys Gly Leu
            20


<210> SEQ ID NO 9
<211> LENGTH: 17
<212> TYPE: PRT
<213> ORGANISM: Artificial Sequence
<220> FEATURE:
<223> OTHER INFORMATION: modified canine

<400> SEQUENCE: 9

Pro Lys Glu Ser Thr Cys Lys Cys Ile Pro Pro Cys Pro Val Pro Glu
1               5                   10                  15

Ser


<210> SEQ ID NO 10
<211> LENGTH: 214
<212> TYPE: PRT
<213> ORGANISM: Artificial Sequence
<220> FEATURE:
<223> OTHER INFORMATION: modified canine

<400> SEQUENCE: 10

Leu Gly Gly Pro Ser Val Phe Ile Phe Pro Pro Lys Pro Lys Asp Thr
1               5                   10                  15

Leu Leu Ile Ala Arg Thr Pro Glu Val Thr Cys Val Val Val Ala Leu
            20                  25                  30

Asp Pro Glu Asp Pro Glu Val Gln Ile Ser Trp Phe Val Asp Gly Lys
        35                  40                  45

Gln Met Gln Thr Ala Lys Thr Gln Pro Arg Glu Glu Gln Phe Ala Gly
    50                  55                  60

Thr Tyr Arg Val Val Ser Val Leu Pro Ile Gly His Gln Asp Trp Leu
65                  70                  75                  80

Lys Gly Lys Gln Phe Thr Cys Lys Val Asn Asn Lys Ala Leu Pro Ser
                85                  90                  95

Pro Ile Glu Arg Thr Ile Ser Lys Ala Arg Gly Gln Ala His Gln Pro
            100                 105                 110

Ser Val Tyr Val Leu Pro Pro Ser Arg Glu Glu Leu Ser Lys Asn Thr
```

-continued

```
        115                 120                 125

Val Ser Leu Thr Cys Leu Ile Lys Asp Phe Phe Pro Pro Asp Ile Asp
    130                 135                 140

Val Glu Trp Gln Ser Asn Gly Gln Gln Glu Pro Glu Ser Lys Tyr Arg
145                 150                 155                 160

Thr Thr Pro Pro Gln Leu Asp Glu Asp Gly Ser Tyr Phe Leu Tyr Ser
                165                 170                 175

Lys Leu Ser Val Asp Lys Ser Arg Trp Gln Arg Gly Asp Thr Phe Ile
            180                 185                 190

Cys Ala Val Met His Glu Ala Leu His Asn His Tyr Thr Gln Glu Ser
        195                 200                 205

Leu Ser His Ser Pro Gly
    210


<210> SEQ ID NO 11
<211> LENGTH: 15
<212> TYPE: DNA
<213> ORGANISM: Artificial Sequence
<220> FEATURE:
<223> OTHER INFORMATION: computer generated based on the amino acid
      sequence of the CDR

<400> SEQUENCE: 11

agatactgga tgcac                                                        15


<210> SEQ ID NO 12
<211> LENGTH: 5
<212> TYPE: PRT
<213> ORGANISM: Mus musculus

<400> SEQUENCE: 12

Arg Tyr Trp Met His
1               5


<210> SEQ ID NO 13
<211> LENGTH: 51
<212> TYPE: DNA
<213> ORGANISM: Artificial Sequence
<220> FEATURE:
<223> OTHER INFORMATION: computer generated based on the amino acid
      sequence of the CDR

<400> SEQUENCE: 13

atgattcacc ccgacagcgg caacatcaac tacaacgagc ggttcaagac c                51


<210> SEQ ID NO 14
<211> LENGTH: 17
<212> TYPE: PRT
<213> ORGANISM: Mus musculus

<400> SEQUENCE: 14

Met Ile His Pro Asp Ser Gly Asn Ile Asn Tyr Asn Glu Arg Phe Lys
1               5                   10                  15

Thr


<210> SEQ ID NO 15
<211> LENGTH: 24
<212> TYPE: DNA
<213> ORGANISM: Artificial Sequence
<220> FEATURE:
<223> OTHER INFORMATION: computer generated based on the amino acid
      sequence of the CDR
```

<400> SEQUENCE: 15
cagctgcgga acgccatgga ttat 24

<210> SEQ ID NO 16
<211> LENGTH: 8
<212> TYPE: PRT
<213> ORGANISM: Mus musculus

<400> SEQUENCE: 16

Gln Leu Arg Asn Ala Met Asp Tyr
1 5

<210> SEQ ID NO 17
<211> LENGTH: 45
<212> TYPE: DNA
<213> ORGANISM: Artificial Sequence
<220> FEATURE:
<223> OTHER INFORMATION: computer generated based on the amino acid sequence of the CDR

<400> SEQUENCE: 17
agagccagcg agagcgtgga cagctacggc aacagcttcc tgaac 45

<210> SEQ ID NO 18
<211> LENGTH: 15
<212> TYPE: PRT
<213> ORGANISM: Mus musculus

<400> SEQUENCE: 18

Arg Ala Ser Glu Ser Val Asp Ser Tyr Gly Asn Ser Phe Leu Asn
1 5 10 15

<210> SEQ ID NO 19
<211> LENGTH: 21
<212> TYPE: DNA
<213> ORGANISM: Artificial Sequence
<220> FEATURE:
<223> OTHER INFORMATION: computer generated based on the amino acid sequence of the CDR

<400> SEQUENCE: 19
agagccagca acctggcctc t 21

<210> SEQ ID NO 20
<211> LENGTH: 7
<212> TYPE: PRT
<213> ORGANISM: Mus musculus

<400> SEQUENCE: 20

Arg Ala Ser Asn Leu Ala Ser
1 5

<210> SEQ ID NO 21
<211> LENGTH: 27
<212> TYPE: DNA
<213> ORGANISM: Artificial Sequence
<220> FEATURE:
<223> OTHER INFORMATION: computer generated based on the amino acid sequence of the CDR

<400> SEQUENCE: 21
cagcagaact acgagaaccc cagaacc 27

<210> SEQ ID NO 22
<211> LENGTH: 9

-continued

```
<212> TYPE: PRT
<213> ORGANISM: Mus musculus

<400> SEQUENCE: 22

Gln Gln Asn Tyr Glu Asn Pro Arg Thr
1               5


<210> SEQ ID NO 23
<211> LENGTH: 15
<212> TYPE: DNA
<213> ORGANISM: Artificial Sequence
<220> FEATURE:
<223> OTHER INFORMATION: computer generated based on the amino acid
      sequence of the CDR

<400> SEQUENCE: 23

agctacggca tgagc                                                      15


<210> SEQ ID NO 24
<211> LENGTH: 5
<212> TYPE: PRT
<213> ORGANISM: Mus musculus

<400> SEQUENCE: 24

Ser Tyr Gly Met Ser
1               5


<210> SEQ ID NO 25
<211> LENGTH: 51
<212> TYPE: DNA
<213> ORGANISM: Artificial Sequence
<220> FEATURE:
<223> OTHER INFORMATION: computer generated based on the amino acid
      sequence of the CDR

<400> SEQUENCE: 25

acaatcagca gaggcggcga ctacacctac tatcccgaca gcgtgaaggg c              51


<210> SEQ ID NO 26
<211> LENGTH: 17
<212> TYPE: PRT
<213> ORGANISM: Mus musculus

<400> SEQUENCE: 26

Thr Ile Ser Arg Gly Gly Asp Tyr Thr Tyr Tyr Pro Asp Ser Val Lys
1               5                   10                  15

Gly


<210> SEQ ID NO 27
<211> LENGTH: 30
<212> TYPE: DNA
<213> ORGANISM: Artificial Sequence
<220> FEATURE:
<223> OTHER INFORMATION: computer generated based on the amino acid
      sequence of the CDR

<400> SEQUENCE: 27

ggcaccctga acaaccgggg ctttgcttct                                      30


<210> SEQ ID NO 28
<211> LENGTH: 10
<212> TYPE: PRT
<213> ORGANISM: Artificial Sequence
<220> FEATURE:
<223> OTHER INFORMATION: modified murine
```

<400> SEQUENCE: 28

Gly Thr Leu Asn Asn Arg Gly Phe Ala Ser
1 5 10

<210> SEQ ID NO 29
<211> LENGTH: 33
<212> TYPE: DNA
<213> ORGANISM: Artificial Sequence
<220> FEATURE:
<223> OTHER INFORMATION: computer generated based on the amino acid sequence of the CDR

<400> SEQUENCE: 29
aaggccagcc agaacgtggg caccaatgtg gcc 33

<210> SEQ ID NO 30
<211> LENGTH: 11
<212> TYPE: PRT
<213> ORGANISM: Mus musculus

<400> SEQUENCE: 30

Lys Ala Ser Gln Asn Val Gly Thr Asn Val Ala
1 5 10

<210> SEQ ID NO 31
<211> LENGTH: 21
<212> TYPE: DNA
<213> ORGANISM: Artificial Sequence
<220> FEATURE:
<223> OTHER INFORMATION: computer generated based on the amino acid sequence of the CDR

<400> SEQUENCE: 31
agcgccagct accggtactc t 21

<210> SEQ ID NO 32
<211> LENGTH: 7
<212> TYPE: PRT
<213> ORGANISM: Mus musculus

<400> SEQUENCE: 32

Ser Ala Ser Tyr Arg Tyr Ser
1 5

<210> SEQ ID NO 33
<211> LENGTH: 27
<212> TYPE: DNA
<213> ORGANISM: Artificial Sequence
<220> FEATURE:
<223> OTHER INFORMATION: computer generated based on the amino acid sequence of the CDR

<400> SEQUENCE: 33
cagcagtaca acagctaccc ctacacc 27

<210> SEQ ID NO 34
<211> LENGTH: 9
<212> TYPE: PRT
<213> ORGANISM: Mus musculus

<400> SEQUENCE: 34

Gln Gln Tyr Asn Ser Tyr Pro Tyr Thr
1 5

<210> SEQ ID NO 35

<211> LENGTH: 217
<212> TYPE: PRT
<213> ORGANISM: Artificial Sequence
<220> FEATURE:
<223> OTHER INFORMATION: caninized murine

<400> SEQUENCE: 35

```
Glu Ile Val Met Thr Gln Ser Pro Ala Ser Leu Ser Leu Ser Gln Glu
1               5                   10                  15

Glu Lys Val Thr Ile Thr Cys Lys Ala Ser Gln Asn Val Gly Thr Asn
            20                  25                  30

Val Ala Trp Tyr Gln Gln Lys Pro Gly Gln Ala Pro Lys Leu Leu Ile
        35                  40                  45

Tyr Ser Ala Ser Tyr Arg Tyr Ser Gly Leu Pro Asp Arg Phe Ser Gly
    50                  55                  60

Ser Gly Ser Gly Thr Asp Phe Ser Phe Thr Ile Ser Ser Leu Glu Pro
65                  70                  75                  80

Glu Asp Val Ala Glu Phe Phe Cys Gln Gln Tyr Asn Ser Tyr Pro Tyr
                85                  90                  95

Thr Phe Gly Gln Gly Thr Lys Leu Glu Ile Lys Arg Asn Asp Ala Gln
            100                 105                 110

Pro Ala Val Tyr Leu Phe Gln Pro Ser Pro Asp Gln Leu His Thr Gly
        115                 120                 125

Ser Ala Ser Val Val Cys Leu Leu Asn Ser Phe Tyr Pro Lys Asp Ile
    130                 135                 140

Asn Val Lys Trp Lys Val Asp Gly Val Ile Gln Asp Thr Gly Ile Gln
145                 150                 155                 160

Glu Ser Val Thr Glu Gln Asp Lys Asp Ser Thr Tyr Ser Leu Ser Ser
                165                 170                 175

Thr Leu Thr Met Ser Ser Thr Glu Tyr Leu Ser His Glu Leu Tyr Ser
            180                 185                 190

Cys Glu Ile Thr His Lys Ser Leu Pro Ser Thr Leu Ile Lys Ser Phe
        195                 200                 205

Gln Arg Ser Glu Cys Gln Arg Val Asp
    210                 215
```

<210> SEQ ID NO 36
<211> LENGTH: 453
<212> TYPE: PRT
<213> ORGANISM: Artificial Sequence
<220> FEATURE:
<223> OTHER INFORMATION: caninized murine

<400> SEQUENCE: 36

```
Glu Val Gln Leu Val Glu Ser Gly Gly Asp Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Gln Trp Val
        35                  40                  45

Ala Thr Ile Ser Arg Gly Gly Asp Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Lys Gly Thr Leu Asn Asn Arg Gly Phe Ala Cys Trp Gly Gln Gly
```

-continued

```
            100                 105                 110

Thr Leu Val Thr Val Ser Ser Ala Ser Thr Thr Ala Pro Ser Val Phe
        115                 120                 125

Pro Leu Ala Pro Ser Cys Gly Ser Thr Ser Gly Ser Thr Val Ala Leu
    130                 135                 140

Ala Cys Leu Val Ser Gly Tyr Phe Pro Glu Pro Val Thr Val Ser Trp
145                 150                 155                 160

Asn Ser Gly Ser Leu Thr Ser Gly Val His Thr Phe Pro Ser Val Leu
                165                 170                 175

Gln Ser Ser Gly Leu Tyr Ser Leu Ser Ser Met Val Thr Val Pro Ser
            180                 185                 190

Ser Arg Trp Pro Ser Glu Thr Phe Thr Cys Asn Val Ala His Pro Ala
        195                 200                 205

Ser Lys Thr Lys Val Asp Lys Pro Val Pro Lys Arg Glu Asn Gly Arg
    210                 215                 220

Val Pro Arg Pro Pro Asp Cys Pro Lys Cys Pro Ala Pro Glu Met Leu
225                 230                 235                 240

Gly Gly Pro Ser Val Phe Ile Phe Pro Pro Lys Pro Lys Asp Thr Leu
                245                 250                 255

Leu Ile Ala Arg Thr Pro Glu Val Thr Cys Val Val Val Ala Leu Asp
            260                 265                 270

Pro Glu Asp Pro Glu Val Gln Ile Ser Trp Phe Val Asp Gly Lys Gln
        275                 280                 285

Met Gln Thr Ala Lys Thr Gln Pro Arg Glu Glu Gln Phe Ala Gly Thr
    290                 295                 300

Tyr Arg Val Val Ser Val Leu Pro Ile Gly His Gln Asp Trp Leu Lys
305                 310                 315                 320

Gly Lys Gln Phe Thr Cys Lys Val Asn Asn Lys Ala Leu Pro Ser Pro
                325                 330                 335

Ile Glu Arg Thr Ile Ser Lys Ala Arg Gly Gln Ala His Gln Pro Ser
            340                 345                 350

Val Tyr Val Leu Pro Pro Ser Arg Glu Glu Leu Ser Lys Asn Thr Val
        355                 360                 365

Ser Leu Thr Cys Leu Ile Lys Asp Phe Phe Pro Pro Asp Ile Asp Val
    370                 375                 380

Glu Trp Gln Ser Asn Gly Gln Gln Glu Pro Glu Ser Lys Tyr Arg Thr
385                 390                 395                 400

Thr Pro Pro Gln Leu Asp Glu Asp Gly Ser Tyr Phe Leu Tyr Ser Lys
                405                 410                 415

Leu Ser Val Asp Lys Ser Arg Trp Gln Arg Gly Asp Thr Phe Ile Cys
            420                 425                 430

Ala Val Met His Glu Ala Leu His Asn His Tyr Thr Gln Glu Ser Leu
        435                 440                 445

Ser His Ser Pro Gly
    450


<210> SEQ ID NO 37
<211> LENGTH: 453
<212> TYPE: PRT
<213> ORGANISM: Artificial Sequence
<220> FEATURE:
<223> OTHER INFORMATION: caninized murine

<400> SEQUENCE: 37

Glu Val Gln Leu Val Glu Ser Gly Gly Asp Leu Val Lys Pro Gly Gly
```

-continued

```
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Asp Lys Arg Leu Gln Trp Val
        35                  40                  45

Ala Thr Ile Ser Arg Gly Gly Asp Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Gly Thr Leu Asn Asn Arg Gly Phe Ala Cys Trp Gly Gln Gly
            100                 105                 110

Thr Leu Val Thr Val Ser Ser Ala Ser Thr Thr Ala Pro Ser Val Phe
        115                 120                 125

Pro Leu Ala Pro Ser Cys Gly Ser Thr Ser Gly Ser Thr Val Ala Leu
    130                 135                 140

Ala Cys Leu Val Ser Gly Tyr Phe Pro Glu Pro Val Thr Val Ser Trp
145                 150                 155                 160

Asn Ser Gly Ser Leu Thr Ser Gly Val His Thr Phe Pro Ser Val Leu
                165                 170                 175

Gln Ser Ser Gly Leu Tyr Ser Leu Ser Ser Met Val Thr Val Pro Ser
            180                 185                 190

Ser Arg Trp Pro Ser Glu Thr Phe Thr Cys Asn Val Ala His Pro Ala
        195                 200                 205

Ser Lys Thr Lys Val Asp Lys Pro Val Pro Lys Arg Glu Asn Gly Arg
    210                 215                 220

Val Pro Arg Pro Pro Asp Cys Pro Lys Cys Pro Ala Pro Glu Met Leu
225                 230                 235                 240

Gly Gly Pro Ser Val Phe Ile Phe Pro Pro Lys Pro Lys Asp Thr Leu
                245                 250                 255

Leu Ile Ala Arg Thr Pro Glu Val Thr Cys Val Val Val Ala Leu Asp
            260                 265                 270

Pro Glu Asp Pro Glu Val Gln Ile Ser Trp Phe Val Asp Gly Lys Gln
        275                 280                 285

Met Gln Thr Ala Lys Thr Gln Pro Arg Glu Glu Gln Phe Ala Gly Thr
    290                 295                 300

Tyr Arg Val Val Ser Val Leu Pro Ile Gly His Gln Asp Trp Leu Lys
305                 310                 315                 320

Gly Lys Gln Phe Thr Cys Lys Val Asn Asn Lys Ala Leu Pro Ser Pro
                325                 330                 335

Ile Glu Arg Thr Ile Ser Lys Ala Arg Gly Gln Ala His Gln Pro Ser
            340                 345                 350

Val Tyr Val Leu Pro Pro Ser Arg Glu Glu Leu Ser Lys Asn Thr Val
        355                 360                 365

Ser Leu Thr Cys Leu Ile Lys Asp Phe Phe Pro Pro Asp Ile Asp Val
    370                 375                 380

Glu Trp Gln Ser Asn Gly Gln Gln Glu Pro Glu Ser Lys Tyr Arg Thr
385                 390                 395                 400

Thr Pro Pro Gln Leu Asp Glu Asp Gly Ser Tyr Phe Leu Tyr Ser Lys
                405                 410                 415

Leu Ser Val Asp Lys Ser Arg Trp Gln Arg Gly Asp Thr Phe Ile Cys
            420                 425                 430
```

Ala Val Met His Glu Ala Leu His Asn His Tyr Thr Gln Glu Ser Leu
435 440 445

Ser His Ser Pro Gly
450

<210> SEQ ID NO 38
<211> LENGTH: 453
<212> TYPE: PRT
<213> ORGANISM: Artificial Sequence
<220> FEATURE:
<223> OTHER INFORMATION: caninized murine

<400> SEQUENCE: 38

Glu Val Gln Leu Val Glu Ser Gly Gly Asp Leu Val Lys Pro Gly Gly
1 5 10 15

Ser Leu Arg Leu Ser Cys Ala Ala Ser Gly Phe Thr Phe Ser Ser Tyr
20 25 30

Gly Met Ser Trp Val Arg Gln Ala Pro Asp Lys Arg Leu Gln Trp Val
35 40 45

Ala Thr Ile Ser Arg Gly Gly Asp Tyr Thr Tyr Tyr Pro Asp Ser Val
50 55 60

Lys Gly Arg Phe Thr Ile Ser Arg Asp Asn Ala Lys Asn Thr Leu Tyr
65 70 75 80

Leu Gln Met Asn Ser Leu Arg Ala Glu Asp Thr Ala Met Tyr Tyr Cys
85 90 95

Ala Arg Gly Thr Leu Asn Asn Arg Gly Phe Ala Ser Trp Gly Gln Gly
100 105 110

Thr Leu Val Thr Val Ser Ser Ala Ser Thr Thr Ala Pro Ser Val Phe
115 120 125

Pro Leu Ala Pro Ser Cys Gly Ser Thr Ser Gly Ser Thr Val Ala Leu
130 135 140

Ala Cys Leu Val Ser Gly Tyr Phe Pro Glu Pro Val Thr Val Ser Trp
145 150 155 160

Asn Ser Gly Ser Leu Thr Ser Gly Val His Thr Phe Pro Ser Val Leu
165 170 175

Gln Ser Ser Gly Leu Tyr Ser Leu Ser Ser Met Val Thr Val Pro Ser
180 185 190

Ser Arg Trp Pro Ser Glu Thr Phe Thr Cys Asn Val Ala His Pro Ala
195 200 205

Ser Lys Thr Lys Val Asp Lys Pro Val Pro Lys Arg Glu Asn Gly Arg
210 215 220

Val Pro Arg Pro Pro Asp Cys Pro Lys Cys Pro Ala Pro Glu Met Leu
225 230 235 240

Gly Gly Pro Ser Val Phe Ile Phe Pro Pro Lys Pro Lys Asp Thr Leu
245 250 255

Leu Ile Ala Arg Thr Pro Glu Val Thr Cys Val Val Val Ala Leu Asp
260 265 270

Pro Glu Asp Pro Glu Val Gln Ile Ser Trp Phe Val Asp Gly Lys Gln
275 280 285

Met Gln Thr Ala Lys Thr Gln Pro Arg Glu Glu Gln Phe Ala Gly Thr
290 295 300

Tyr Arg Val Val Ser Val Leu Pro Ile Gly His Gln Asp Trp Leu Lys
305 310 315 320

Gly Lys Gln Phe Thr Cys Lys Val Asn Asn Lys Ala Leu Pro Ser Pro
325 330 335

```
Ile Glu Arg Thr Ile Ser Lys Ala Arg Gly Gln Ala His Gln Pro Ser
            340                 345                 350

Val Tyr Val Leu Pro Pro Ser Arg Glu Glu Leu Ser Lys Asn Thr Val
        355                 360                 365

Ser Leu Thr Cys Leu Ile Lys Asp Phe Phe Pro Pro Asp Ile Asp Val
    370                 375                 380

Glu Trp Gln Ser Asn Gly Gln Gln Glu Pro Glu Ser Lys Tyr Arg Thr
385                 390                 395                 400

Thr Pro Pro Gln Leu Asp Glu Asp Gly Ser Tyr Phe Leu Tyr Ser Lys
                405                 410                 415

Leu Ser Val Asp Lys Ser Arg Trp Gln Arg Gly Asp Thr Phe Ile Cys
            420                 425                 430

Ala Val Met His Glu Ala Leu His Asn His Tyr Thr Gln Glu Ser Leu
        435                 440                 445

Ser His Ser Pro Gly
    450


<210> SEQ ID NO 39
<211> LENGTH: 221
<212> TYPE: PRT
<213> ORGANISM: Artificial Sequence
<220> FEATURE:
<223> OTHER INFORMATION: caninized murine

<400> SEQUENCE: 39

Asp Ile Val Leu Thr Gln Thr Pro Leu Ser Leu Ser Val Ser Pro Gly
1               5                   10                  15

Glu Thr Ala Ser Ile Tyr Cys Arg Ala Ser Glu Ser Val Asp Ser Tyr
            20                  25                  30

Gly Asn Ser Phe Leu Asn Trp Tyr Gln Gln Lys Pro Gly Gln Pro Pro
        35                  40                  45

Lys Leu Leu Ile Tyr Arg Ala Ser Asn Leu Ala Ser Glu Ile Pro Asp
    50                  55                  60

Arg Phe Ser Gly Ser Gly Ser Arg Thr Glu Phe Thr Leu Lys Ile Ser
65                  70                  75                  80

Arg Val Glu Ala Asp Asp Ala Gly Val Tyr Tyr Cys Gln Gln Asn Tyr
                85                  90                  95

Glu Asn Pro Arg Thr Phe Gly Gln Gly Thr Lys Leu Glu Ile Lys Arg
            100                 105                 110

Asn Asp Ala Gln Pro Ala Val Tyr Leu Phe Gln Pro Ser Pro Asp Gln
        115                 120                 125

Leu His Thr Gly Ser Ala Ser Val Val Cys Leu Leu Asn Ser Phe Tyr
    130                 135                 140

Pro Lys Asp Ile Asn Val Lys Trp Lys Val Asp Gly Val Ile Gln Asp
145                 150                 155                 160

Thr Gly Ile Gln Glu Ser Val Thr Glu Gln Asp Lys Asp Ser Thr Tyr
                165                 170                 175

Ser Leu Ser Ser Thr Leu Thr Met Ser Ser Thr Glu Tyr Leu Ser His
            180                 185                 190

Glu Leu Tyr Ser Cys Glu Ile Thr His Lys Ser Leu Pro Ser Thr Leu
        195                 200                 205

Ile Lys Ser Phe Gln Arg Ser Glu Cys Gln Arg Val Asp
    210                 215                 220


<210> SEQ ID NO 40
```

<211> LENGTH: 451
<212> TYPE: PRT
<213> ORGANISM: Artificial Sequence
<220> FEATURE:
<223> OTHER INFORMATION: caninized murine

<400> SEQUENCE: 40

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Arg Tyr
            20                  25                  30

Trp Met His Trp Val Arg Gln Ala Pro Gly Ala Gly Leu Asp Trp Met
        35                  40                  45

Gly Met Ile His Pro Asp Ser Gly Asn Ile Asn Tyr Asn Glu Arg Phe
    50                  55                  60

Lys Thr Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gln Leu Arg Asn Ala Met Asp Tyr Trp Gly Gln Gly Thr Leu
            100                 105                 110

Val Thr Val Ser Ser Ala Ser Thr Thr Ala Pro Ser Val Phe Pro Leu
        115                 120                 125

Ala Pro Ser Cys Gly Ser Thr Ser Gly Ser Thr Val Ala Leu Ala Cys
    130                 135                 140

Leu Val Ser Gly Tyr Phe Pro Glu Pro Val Thr Val Ser Trp Asn Ser
145                 150                 155                 160

Gly Ser Leu Thr Ser Gly Val His Thr Phe Pro Ser Val Leu Gln Ser
                165                 170                 175

Ser Gly Leu Tyr Ser Leu Ser Ser Met Val Thr Val Pro Ser Ser Arg
            180                 185                 190

Trp Pro Ser Glu Thr Phe Thr Cys Asn Val Ala His Pro Ala Ser Lys
        195                 200                 205

Thr Lys Val Asp Lys Pro Val Pro Lys Arg Glu Asn Gly Arg Val Pro
    210                 215                 220

Arg Pro Pro Asp Cys Pro Lys Cys Pro Ala Pro Glu Met Leu Gly Gly
225                 230                 235                 240

Pro Ser Val Phe Ile Phe Pro Pro Lys Pro Lys Asp Thr Leu Leu Ile
                245                 250                 255

Ala Arg Thr Pro Glu Val Thr Cys Val Val Val Ala Leu Asp Pro Glu
            260                 265                 270

Asp Pro Glu Val Gln Ile Ser Trp Phe Val Asp Gly Lys Gln Met Gln
        275                 280                 285

Thr Ala Lys Thr Gln Pro Arg Glu Glu Gln Phe Ala Gly Thr Tyr Arg
    290                 295                 300

Val Val Ser Val Leu Pro Ile Gly His Gln Asp Trp Leu Lys Gly Lys
305                 310                 315                 320

Gln Phe Thr Cys Lys Val Asn Asn Lys Ala Leu Pro Ser Pro Ile Glu
                325                 330                 335

Arg Thr Ile Ser Lys Ala Arg Gly Gln Ala His Gln Pro Ser Val Tyr
            340                 345                 350

Val Leu Pro Pro Ser Arg Glu Glu Leu Ser Lys Asn Thr Val Ser Leu
        355                 360                 365

Thr Cys Leu Ile Lys Asp Phe Phe Pro Pro Asp Ile Asp Val Glu Trp
    370                 375                 380
```

-continued

Gln Ser Asn Gly Gln Gln Glu Pro Glu Ser Lys Tyr Arg Thr Thr Pro
385 390 395 400

Pro Gln Leu Asp Glu Asp Gly Ser Tyr Phe Leu Tyr Ser Lys Leu Ser
405 410 415

Val Asp Lys Ser Arg Trp Gln Arg Gly Asp Thr Phe Ile Cys Ala Val
420 425 430

Met His Glu Ala Leu His Asn His Tyr Thr Gln Glu Ser Leu Ser His
435 440 445

Ser Pro Gly
450

<210> SEQ ID NO 41
<211> LENGTH: 451
<212> TYPE: PRT
<213> ORGANISM: Artificial Sequence
<220> FEATURE:
<223> OTHER INFORMATION: caninized murine

<400> SEQUENCE: 41

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Ala Arg Tyr
20 25 30

Trp Met His Trp Met Lys Gln Ala Pro Gly Ala Gly Leu Asp Trp Ile
35 40 45

Gly Met Ile His Pro Asp Ser Gly Asn Ile Asn Tyr Asn Glu Arg Phe
50 55 60

Lys Thr Lys Ala Thr Leu Thr Ala Asp Thr Ser Thr Ser Thr Ala Tyr
65 70 75 80

Met Glu Leu Ser Ser Leu Arg Ala Gly Asp Ile Ala Val Tyr Tyr Cys
85 90 95

Ala Arg Gln Leu Arg Asn Ala Met Asp Tyr Trp Gly Gln Gly Thr Leu
100 105 110

Val Thr Val Ser Ser Ala Ser Thr Thr Ala Pro Ser Val Phe Pro Leu
115 120 125

Ala Pro Ser Cys Gly Ser Thr Ser Gly Ser Thr Val Ala Leu Ala Cys
130 135 140

Leu Val Ser Gly Tyr Phe Pro Glu Pro Val Thr Val Ser Trp Asn Ser
145 150 155 160

Gly Ser Leu Thr Ser Gly Val His Thr Phe Pro Ser Val Leu Gln Ser
165 170 175

Ser Gly Leu Tyr Ser Leu Ser Ser Met Val Thr Val Pro Ser Ser Arg
180 185 190

Trp Pro Ser Glu Thr Phe Thr Cys Asn Val Ala His Pro Ala Ser Lys
195 200 205

Thr Lys Val Asp Lys Pro Val Pro Lys Arg Glu Asn Gly Arg Val Pro
210 215 220

Arg Pro Pro Asp Cys Pro Lys Cys Pro Ala Pro Glu Met Leu Gly Gly
225 230 235 240

Pro Ser Val Phe Ile Phe Pro Pro Lys Pro Lys Asp Thr Leu Leu Ile
245 250 255

Ala Arg Thr Pro Glu Val Thr Cys Val Val Val Ala Leu Asp Pro Glu
260 265 270

Asp Pro Glu Val Gln Ile Ser Trp Phe Val Asp Gly Lys Gln Met Gln
275 280 285

Thr Ala Lys Thr Gln Pro Arg Glu Glu Gln Phe Ala Gly Thr Tyr Arg
290 295 300

Val Val Ser Val Leu Pro Ile Gly His Gln Asp Trp Leu Lys Gly Lys
305 310 315 320

Gln Phe Thr Cys Lys Val Asn Asn Lys Ala Leu Pro Ser Pro Ile Glu
325 330 335

Arg Thr Ile Ser Lys Ala Arg Gly Gln Ala His Gln Pro Ser Val Tyr
340 345 350

Val Leu Pro Pro Ser Arg Glu Glu Leu Ser Lys Asn Thr Val Ser Leu
355 360 365

Thr Cys Leu Ile Lys Asp Phe Phe Pro Pro Asp Ile Asp Val Glu Trp
370 375 380

Gln Ser Asn Gly Gln Gln Glu Pro Glu Ser Lys Tyr Arg Thr Thr Pro
385 390 395 400

Pro Gln Leu Asp Glu Asp Gly Ser Tyr Phe Leu Tyr Ser Lys Leu Ser
405 410 415

Val Asp Lys Ser Arg Trp Gln Arg Gly Asp Thr Phe Ile Cys Ala Val
420 425 430

Met His Glu Ala Leu His Asn His Tyr Thr Gln Glu Ser Leu Ser His
435 440 445

Ser Pro Gly
450

<210> SEQ ID NO 42
<211> LENGTH: 451
<212> TYPE: PRT
<213> ORGANISM: Artificial Sequence
<220> FEATURE:
<223> OTHER INFORMATION: caninized murine

<400> SEQUENCE: 42

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Ala Arg Tyr
20 25 30

Trp Met His Trp Met Lys Gln Ala Pro Gly Ala Gly Leu Asp Trp Ile
35 40 45

Gly Met Ile His Pro Asp Ser Gly Asn Ile Asn Tyr Asn Glu Arg Phe
50 55 60

Lys Thr Lys Ala Thr Leu Thr Val Asp Lys Ser Thr Ser Thr Ala Tyr
65 70 75 80

Met Glu Leu Ser Ser Leu Arg Ala Gly Asp Ile Ala Val Tyr Tyr Cys
85 90 95

Ala Arg Gln Leu Arg Asn Ala Met Asp Tyr Trp Gly Gln Gly Thr Leu
100 105 110

Val Thr Val Ser Ser Ala Ser Thr Thr Ala Pro Ser Val Phe Pro Leu
115 120 125

Ala Pro Ser Cys Gly Ser Thr Ser Gly Ser Thr Val Ala Leu Ala Cys
130 135 140

Leu Val Ser Gly Tyr Phe Pro Glu Pro Val Thr Val Ser Trp Asn Ser
145 150 155 160

Gly Ser Leu Thr Ser Gly Val His Thr Phe Pro Ser Val Leu Gln Ser
165 170 175

Ser Gly Leu Tyr Ser Leu Ser Ser Met Val Thr Val Pro Ser Ser Arg
180 185 190

Trp Pro Ser Glu Thr Phe Thr Cys Asn Val Ala His Pro Ala Ser Lys
195 200 205

Thr Lys Val Asp Lys Pro Val Pro Lys Arg Glu Asn Gly Arg Val Pro
210 215 220

Arg Pro Pro Asp Cys Pro Lys Cys Pro Ala Pro Glu Met Leu Gly Gly
225 230 235 240

Pro Ser Val Phe Ile Phe Pro Pro Lys Pro Lys Asp Thr Leu Leu Ile
245 250 255

Ala Arg Thr Pro Glu Val Thr Cys Val Val Val Ala Leu Asp Pro Glu
260 265 270

Asp Pro Glu Val Gln Ile Ser Trp Phe Val Asp Gly Lys Gln Met Gln
275 280 285

Thr Ala Lys Thr Gln Pro Arg Glu Glu Gln Phe Ala Gly Thr Tyr Arg
290 295 300

Val Val Ser Val Leu Pro Ile Gly His Gln Asp Trp Leu Lys Gly Lys
305 310 315 320

Gln Phe Thr Cys Lys Val Asn Asn Lys Ala Leu Pro Ser Pro Ile Glu
325 330 335

Arg Thr Ile Ser Lys Ala Arg Gly Gln Ala His Gln Pro Ser Val Tyr
340 345 350

Val Leu Pro Pro Ser Arg Glu Glu Leu Ser Lys Asn Thr Val Ser Leu
355 360 365

Thr Cys Leu Ile Lys Asp Phe Phe Pro Pro Asp Ile Asp Val Glu Trp
370 375 380

Gln Ser Asn Gly Gln Gln Glu Pro Glu Ser Lys Tyr Arg Thr Thr Pro
385 390 395 400

Pro Gln Leu Asp Glu Asp Gly Ser Tyr Phe Leu Tyr Ser Lys Leu Ser
405 410 415

Val Asp Lys Ser Arg Trp Gln Arg Gly Asp Thr Phe Ile Cys Ala Val
420 425 430

Met His Glu Ala Leu His Asn His Tyr Thr Gln Glu Ser Leu Ser His
435 440 445

Ser Pro Gly
450

<210> SEQ ID NO 43
<211> LENGTH: 212
<212> TYPE: PRT
<213> ORGANISM: Artificial Sequence
<220> FEATURE:
<223> OTHER INFORMATION: caninized murine

<400> SEQUENCE: 43

Gln Ser Val Leu Thr Gln Pro Ala Ser Val Ser Gly Ser Leu Gly Gln
1 5 10 15

Arg Val Thr Ile Ser Cys Lys Ala Ser Gln Asn Val Gly Thr Asn Val
20 25 30

Ala Trp Tyr Gln Gln Leu Pro Gly Thr Ser Pro Arg Thr Leu Ile Tyr
35 40 45

Ser Ala Ser Tyr Arg Tyr Ser Gly Val Pro Asp Arg Phe Ser Gly Ser
50 55 60

Arg Ser Gly Ser Thr Ala Thr Leu Thr Ile Ser Gly Leu Gln Ala Glu
65 70 75 80

Asp Glu Ala Asp Tyr Tyr Cys Gln Gln Tyr Asn Ser Tyr Pro Tyr Thr
85 90 95

```
Phe Gly Gly Gly Thr His Leu Thr Val Leu Gly Gln Pro Lys Ala Ser
            100                 105                 110

Pro Ser Val Thr Leu Phe Pro Pro Ser Ser Glu Glu Leu Gly Ala Asn
        115                 120                 125

Lys Ala Thr Leu Val Cys Leu Ile Ser Asp Phe Tyr Pro Ser Gly Val
    130                 135                 140

Thr Val Ala Trp Lys Ala Asp Gly Ser Pro Val Thr Gln Gly Val Glu
145                 150                 155                 160

Thr Thr Lys Pro Ser Lys Gln Ser Asn Asn Lys Tyr Ala Ala Ser Ser
                165                 170                 175

Tyr Leu Ser Leu Thr Pro Asp Lys Trp Lys Ser His Ser Ser Phe Ser
            180                 185                 190

Cys Leu Val Thr His Glu Gly Ser Thr Val Glu Lys Lys Val Ala Pro
        195                 200                 205

Ala Glu Cys Ser
    210


<210> SEQ ID NO 44
<211> LENGTH: 216
<212> TYPE: PRT
<213> ORGANISM: Artificial Sequence
<220> FEATURE:
<223> OTHER INFORMATION: caninized murine

<400> SEQUENCE: 44

Gln Ser Val Leu Thr Gln Pro Ala Ser Val Ser Gly Ser Leu Gly Gln
1               5                   10                  15

Arg Val Thr Ile Ser Cys Arg Ala Ser Glu Ser Val Asp Ser Tyr Gly
            20                  25                  30

Asn Ser Phe Leu Asn Trp Tyr Gln Gln Leu Pro Gly Lys Ala Pro Ser
        35                  40                  45

Leu Leu Ile Tyr Arg Ala Ser Asn Leu Ala Ser Gly Val Pro Glu Arg
    50                  55                  60

Phe Ser Gly Ser Lys Ser Gly Ser Ser Ala Thr Leu Thr Ile Thr Gly
65                  70                  75                  80

Leu Gln Ala Glu Asp Glu Ala Asp Tyr Tyr Cys Gln Gln Asn Tyr Glu
                85                  90                  95

Asn Pro Arg Thr Phe Gly Gly Gly Thr His Leu Thr Val Leu Gly Gln
            100                 105                 110

Pro Lys Ala Ser Pro Ser Val Thr Leu Phe Pro Pro Ser Ser Glu Glu
        115                 120                 125

Leu Gly Ala Asn Lys Ala Thr Leu Val Cys Leu Ile Ser Asp Phe Tyr
    130                 135                 140

Pro Ser Gly Val Thr Val Ala Trp Lys Ala Asp Gly Ser Pro Val Thr
145                 150                 155                 160

Gln Gly Val Glu Thr Thr Lys Pro Ser Lys Gln Ser Asn Asn Lys Tyr
                165                 170                 175

Ala Ala Ser Ser Tyr Leu Ser Leu Thr Pro Asp Lys Trp Lys Ser His
            180                 185                 190

Ser Ser Phe Ser Cys Leu Val Thr His Glu Gly Ser Thr Val Glu Lys
        195                 200                 205

Lys Val Ala Pro Ala Glu Cys Ser
    210                 215


<210> SEQ ID NO 45
```

-continued

<211> LENGTH: 215
<212> TYPE: PRT
<213> ORGANISM: Canis familiaris

<400> SEQUENCE: 45

Leu Gly Gly Pro Ser Val Phe Ile Phe Pro Pro Lys Pro Lys Asp Thr
1 5 10 15

Leu Leu Ile Ala Arg Thr Pro Glu Val Thr Cys Val Val Val Asp Leu
20 25 30

Asp Pro Glu Asp Pro Glu Val Gln Ile Ser Trp Phe Val Asp Gly Lys
35 40 45

Gln Met Gln Thr Ala Lys Thr Gln Pro Arg Glu Glu Gln Phe Asn Gly
50 55 60

Thr Tyr Arg Val Val Ser Val Leu Pro Ile Gly His Gln Asp Trp Leu
65 70 75 80

Lys Gly Lys Gln Phe Thr Cys Lys Val Asn Asn Lys Ala Leu Pro Ser
85 90 95

Pro Ile Glu Arg Thr Ile Ser Lys Ala Arg Gly Gln Ala His Gln Pro
100 105 110

Ser Val Tyr Val Leu Pro Pro Ser Arg Glu Glu Leu Ser Lys Asn Thr
115 120 125

Val Ser Leu Thr Cys Leu Ile Lys Asp Phe Phe Pro Pro Asp Ile Asp
130 135 140

Val Glu Trp Gln Ser Asn Gly Gln Gln Glu Pro Glu Ser Lys Tyr Arg
145 150 155 160

Thr Thr Pro Pro Gln Leu Asp Glu Asp Gly Ser Tyr Phe Leu Tyr Ser
165 170 175

Lys Leu Ser Val Asp Lys Ser Arg Trp Gln Arg Gly Asp Thr Phe Ile
180 185 190

Cys Ala Val Met His Glu Ala Leu His Asn His Tyr Thr Gln Lys Ser
195 200 205

Leu Ser His Ser Pro Gly Lys
210 215

<210> SEQ ID NO 46
<211> LENGTH: 31
<212> TYPE: PRT
<213> ORGANISM: Canis familiaris

<400> SEQUENCE: 46

Phe Gln Pro Ser Lys His Val Lys Pro Arg Thr Pro Gly Asn Leu Thr
1 5 10 15

Val His Pro Asn Ile Ser His Thr Trp Leu Leu Met Trp Thr Asn
20 25 30

<210> SEQ ID NO 47
<211> LENGTH: 21
<212> TYPE: PRT
<213> ORGANISM: Canis familiaris

<400> SEQUENCE: 47

Arg Leu Ala Ala Ser Thr Leu Lys Ser Gly Ala Ser Tyr Ser Ala Arg
1 5 10 15

Val Arg Ala Trp Ala
20